(12) United States Patent
Papoutsakis et al.

(10) Patent No.: US 10,640,746 B2
(45) Date of Patent: May 5, 2020

(54) SYNTHETIC METHYLOTROPHS

(71) Applicant: UNIVERSITY OF DELAWARE, Newark, DE (US)

(72) Inventors: Eleftherios T. Papoutsakis, Newark, DE (US); William Brian Whitaker, Wilmington, DE (US); Robert Kyle Bennett, Elkton, MD (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 16/070,318

(22) PCT Filed: Jan. 13, 2017

(86) PCT No.: PCT/US2017/013413
§ 371 (c)(1),
(2) Date: Jul. 16, 2018

(87) PCT Pub. No.: WO2017/123930
PCT Pub. Date: Jul. 20, 2017

(65) Prior Publication Data
US 2019/0024040 A1 Jan. 24, 2019

Related U.S. Application Data

(60) Provisional application No. 62/279,066, filed on Jan. 15, 2016.

(51) Int. Cl.
| | |
|---|---|
| *C12N 1/32* | (2006.01) |
| *C12R 1/15* | (2006.01) |
| *C12R 1/19* | (2006.01) |
| *C12N 9/04* | (2006.01) |
| *C12N 15/52* | (2006.01) |

(52) U.S. Cl.
CPC ............ *C12N 1/32* (2013.01); *C12N 9/0006* (2013.01); *C12N 15/52* (2013.01); *C12R 1/15* (2013.01); *C12R 1/19* (2013.01); *C12Y 101/01244* (2013.01)

(58) Field of Classification Search
CPC ........ C12N 15/52; C12N 9/0006; C12N 1/32; C12Y 101/01244; C12R 1/19; C12R 1/15
See application file for complete search history.

(56) References Cited

U.S. PATENT DOCUMENTS

| | | |
|---|---|---|
| 2004/0191875 A1 | 9/2004 | Takeshita et al. |
| 2007/0087423 A1 | 4/2007 | Murakami et al. |

FOREIGN PATENT DOCUMENTS

WO    WO 2015/108777 A1    7/2015

OTHER PUBLICATIONS

Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Kisselev L., Polypeptide release factors in prokaryotes and eukaryotes: same function, different structure. Structure, 2002, vol. 10: 8-9. (Year: 2002).*
LeBmeier et al., Identification two mutations increasing the methanol tolerance of Corynebacterium glutamicum. BMC Microbiol., 2015, vol. 15:213, 11 pages. (Year: 2015).*
Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Witthoff et al., C1 metabolism in Corynebacterium glutamicum: an endogenous pathway for oxidation of methanol to carbon dioxide. Appl. Environ. Microbiol., 2013, vol. 79 (22): 6974-6983. (Year: 2013).*
International Search Report for International Application No. PCT/US2017/013413 dated May 8, 2017 by Brian R. Copenheaver.
International Search Report with Written Opinion for International Application No. PCT/US2017/013413 dated May 8, 2017 by Brian R. Copenheaver.
Krog et al., PLoS One, 8(3):1-11 (2013).
Whitaker et al., Current Opinion in Biotechnology, 33:165-75 (2015).
International Preliminary Report on Patentability with Written Opinion for International Application No. PCT/US2017/013413 dated Jul. 17, 2018 by Agnès Wittmann-Regis.
Kotrbova-Kozak et al., Appl Microbiol Biotechnol, 76:1347-56 (2007).
Krog et al., PLOS One, 8(3):e59188, pp. 1-11 (2013).
Sheehan et al., Biochem J., 252:661-6 (1988).

* cited by examiner

*Primary Examiner* — Ganapathirama Raghu
(74) *Attorney, Agent, or Firm* — RatnerPrestia

(57) ABSTRACT

The present invention provides a non-naturally occurring microbe capable of growing in a medium comprising methanol, comprising a heterologous polynucleotide encoding a heterologous methanol dehydrogenase (MDH) derived from a *Corynebacterium* organism (Cor), wherein the MDH is expressed in the microbe, and wherein the MDH exhibits a Km of no more than 3 mM for methanol. Also provided are uses of the non-naturally occurring microbe for oxidizing methanol and producing a metabolite as well as the preparation of the non-naturally occurring microbe.

18 Claims, 7 Drawing Sheets
Specification includes a Sequence Listing.

SEQUENCE LISTING

```
<160> NUMBER OF SEQ ID NOS: 1

<210> SEQ ID NO 1
<211> LENGTH: 345
<212> TYPE: PRT
<213> ORGANISM: Corynebacterium glutamicum

<400> SEQUENCE: 1

Met Thr Thr Ala Ala Pro Gln Glu Phe Thr Ala Ala Val Val Glu Lys
1               5                   10                  15

Phe Gly His Glu Val Thr Val Lys Asp Ile Asp Leu Pro Lys Pro Gly
                20                  25                  30

Pro Asn Gln Ala Leu Val Lys Val Leu Thr Ser Gly Ile Cys His Thr
            35                  40                  45

Asp Leu His Ala Leu Glu Gly Asp Trp Pro Val Lys Pro Glu Pro Pro
        50                  55                  60

Phe Val Pro Gly His Glu Gly Val Gly Glu Val Val Glu Leu Gly Pro
65                  70                  75                  80

Gly Glu His Asp Val Lys Val Gly Asp Ile Val Gly Asn Ala Trp Leu
                85                  90                  95

Trp Ser Ala Cys Gly Thr Cys Glu Tyr Cys Ile Thr Gly Arg Glu Thr
            100                 105                 110

Gln Cys Asn Glu Ala Glu Tyr Gly Gly Tyr Thr Gln Asn Gly Ser Phe
        115                 120                 125

Gly Gln Tyr Met Leu Val Asp Thr Arg Tyr Ala Ala Arg Ile Pro Asp
    130                 135                 140

Gly Val Asp Tyr Leu Glu Ala Ala Pro Ile Leu Cys Ala Gly Val Thr
145                 150                 155                 160

Val Tyr Lys Ala Leu Lys Val Ser Glu Thr Arg Pro Gly Gln Phe Met
                165                 170                 175

Val Ile Ser Gly Val Gly Gly Leu Gly His Ile Ala Val Gln Tyr Ala
            180                 185                 190

Ala Ala Met Gly Met Arg Val Ile Ala Val Asp Ile Ala Asp Asp Lys
```

-continued

```
            195                 200                 205
Leu Glu Leu Ala Arg Lys His Gly Ala Glu Phe Thr Val Asn Ala Arg
        210                 215                 220

Asn Glu Asp Pro Gly Glu Ala Val Gln Lys Tyr Thr Asn Gly Gly Ala
225                 230                 235                 240

His Gly Val Leu Val Thr Ala Val His Glu Ala Ala Phe Gly Gln Ala
                245                 250                 255

Leu Asp Met Ala Arg Arg Ala Gly Thr Ile Val Phe Asn Gly Leu Pro
                260                 265                 270

Pro Gly Glu Phe Pro Ala Ser Val Phe Asn Ile Val Phe Lys Gly Leu
        275                 280                 285

Thr Ile Arg Gly Ser Leu Val Gly Thr Arg Gln Asp Leu Ala Glu Ala
        290                 295                 300

Leu Asp Phe Phe Ala Arg Gly Leu Ile Lys Pro Thr Val Ser Glu Cys
305                 310                 315                 320

Ser Leu Asp Glu Val Asn Asp Val Leu Asp Arg Met Arg Asn Gly Lys
                325                 330                 335

Ile Asp Gly Arg Val Ala Ile Arg Tyr
                340                 345
```

SYNTHETIC METHYLOTROPHS

CROSS-REFERENCE TO RELATED APPLICATION

This application is a U.S. national phase application of International Application No. PCT/US2017/013413, filed Jan. 13, 2017, claiming the benefit of U.S. Provisional Application No. 62/279,066, filed 15 Jan. 2016, the contents of each of which are incorporated herein by reference in their entireties for all purposes.

REFERENCE TO U.S. GOVERNMENT SUPPORT

This work is supported by a grant from the U.S. Advanced Research Projects Agency-Energy (ARPA-E) of Department of Energy (DOE) (Award No. DE-AR0000432). The United States has certain rights in the invention.

FIELD OF THE INVENTION

The invention relates generally to non-naturally occurring microbes capable of growing in a medium comprising methanol, and the uses thereof for producing desirable liquid fuels and chemicals.

BACKGROUND OF THE INVENTION

Natural gas consists primarily of methane ($CH_4$), and includes smaller amounts of higher alkanes, $CO_2$, $N_2$, and $H_2S$. It is used not only for heating and energy generation, but also as a chemical feedstock to produce commodity chemicals that can be then converted to plastics and specialty chemicals. Natural gas constitutes an enormous energy and chemical resource for the US where the recoverable amount is estimated to be 2,000 trillion $ft^3$. Natural gas is however a poor transportation fuel because of its inherently low energy density. Technologies that can convert natural gas into liquid fuels at competitive prices will not only lessen our dependence on imported oil, but also eliminate the needs for retrofitting existing transportation infrastructure. Current chemical routes based on chemical conversion to syngas (CO & $H_2$) through the Fischer-Tropsch process are not competitive for producing liquid fuels, as they suffer from both high capital costs and low conversion efficiencies. Bioconversion is a promising alternative because of its high specificity and high process energy efficiency all under very mild conditions. Thus, $CH_4$ represents an ideal target for conversion to liquid fuels by biological processes or hybrid biological/catalytic processes.

Some progress has been made in the catalytic conversion of $CH_4$ to methanol (MeOH), more biological means may be developed for converting methane to methanol, likely by a form of reverse methanogenesis. Non-naturally occurring or synthetic microbes expressing a heterologous methanol dehydrogenase (MDH) and other heterologous ribulose monophosphate (RuMP) pathway enzymes have been developed to grow in a medium comprising methanol (see WO 2015/108777 A1), but such heterologous MDH does not operate optimally under normal conditions (e.g., temperature) for microbes such as *Escherichia coli* (*E. coli*) strain commonly used to produce liquid fuel molecules or other commodity chemicals. There remains a need for non-naturally occurring methylotrophic microbes capable of converting methanol efficiently to liquid fuel molecules or other commodity chemicals.

SUMMARY OF THE INVENTION

The present invention relates to non-naturally occurring microbes and methods for use or preparation thereof.

The present invention provides a non-naturally occurring microbe capable of growing in a medium comprising methanol. The non-naturally occurring microbe comprises a heterologous polynucleotide encoding a heterologous methanol dehydrogenase (MDH) derived from a *Corynebacterium* organism (Cor). The MDH is expressed in the microbe. The MDH exhibits a Km of no more than 3 mM for methanol. The methanol in the medium may contribute to at least 40% of the carbon source for the non-naturally occurring microbe.

The MDH may exhibit a Km of no more than 3 mM for methanol at a temperature in a range from 30° C. to 37° C. The MDH may exhibit a Km of no more than 3 mM for methanol at a temperature of 30° C.

The MDH may exhibit a Km of at least 30 mM for butanol.

The Cor may be selected from the group consisting of *Corynebacterium glutamicum*, *Corynebacterium* sp., *Corynebacterium crudilactis*, *Corynebacterium deserti*, *Corynebacterium lubricantis*, *Corynebacterium callunae*, *Corynebacterium stationis*, *Corynebacterium casei*, *Corynebacterium ammoniagenes*, *Corynebacterium amycolatum*, *Corynebacterium* sp. HMSC064E07, *Corynebacterium lactis*, *Corynebacterium* sp. HMSC077G07, *Corynebacterium* sp. HMSC074C05, *Corynebacterium humireducens*, *Corynebacterium resistens*, *Corynebacterium vitaeruminis*, *Corynebacterium durum*, *Corynebacterium ulcerans*, *Corynebacterium ulcerans* FRC11, *Corynebacterium ulcerans* NCTC 12077, *Corynebacterium ulcerans* FRC58, *Corynebacterium efficiens*, *Corynebacterium ulcerans* 0102, *Corynebacterium terpenotabidum*, *Corynebacterium lipophiloflavum*, *Corynebacterium diphtheria*, *Corynebacterium* sp. HMSC034A01, *Corynebacterium* sp. HMSC034B08, *Corynebacterium* sp. HMSC05H05, *Corynebacterium mustelae*, *Corynebacterium* sp. HMSC04H06, *Corynebacterium pseudotuberculosis*, *Corynebacterium* sp. HMSC070H05, *Corynebacterium* sp. HMSC29G08, *Corynebacterium* sp. HMSC11D10, *Corynebacterium kutscheri*, *Corynebacterium freiburgense*, *Corynebacterium pseudotuberculosis* FRC41, *Corynebacterium* sp. HMSC067D03, *Corynebacterium* sp. HMSC036E10, *Corynebacterium jeddahense*, *Corynebacterium ciconiae*, *Corynebacterium coyleae*, *Corynebacterium sputi*, *Corynebacterium tuscaniense*, *Corynebacterium* sp. HMSC074A01, *Corynebacterium variabile*, *Corynebacterium nuruki*, *Corynebacterium testudinoris*, *Corynebacterium striatum*, *Corynebacterium pseudodiphtheriticum*, *Corynebacterium* sp. EPI-003-04-2554_SCH2473622, *Corynebacterium* sp. HMSC06C06, *Corynebacterium* sp. SN15, *Corynebacterium propinquum*, *Corynebacterium* sp. KPL1818, *Corynebacterium* sp. KPL1824, *Corynebacterium timonense*, *Corynebacterium* sp. KPL1824, *Cryobacterium flavum*, *Cryobacterium luteum*, *Cryobacterium levicorallinum*, *Arthrobacter* sp. 162MFSha1.1, *Rothia* sp. ND6WE1A, and *Arthrobacter* sp. Soil761. The Cor may be a *Corynebacterium glutamicum* (Cgl). The Cgl may be *Corynebacterium glutamicum* R (Cgl R).

The MDH may comprise an amino acid sequence at least 70% identical to an amino acid sequence of SEQ ID NO: 1. The MDH may consist of an amino acid sequence of SEQ ID NO: 1.

The non-naturally occurring microbe may further express one or more heterologous ribulose monophosophate (RuMP) pathway enzymes. The expression of the one or more RuMP pathway enzymes may be under control of a formaldehyde responsive promoter. The one or more RuMP pathway enzymes may comprise heterologous 3-hexulose-6-phosphate synthase (HPS) and heterologous 3-hexulose-6-phosphate isomerase (PHI).

The non-naturally occurring microbe may further express one or more heterologous pentose-phosphate pathway (PPP) enzymes. The expression of the one or more heterologous PPP enzymes may be under control of a formaldehyde responsive promoter. The one or more heterologous PPP enzymes may comprise heterologous phosphofructokinase (PFK), heterologous fructose bisphosphate aldolase (FBA), heterologous transketolase (TKT), heterologous fructose/sedoheptulose biphosphatase (GLPX), heterologous transaldolase (TAL), heterologous ribose-5-phosphate isomerase (RPI) and heterologous ribulose phosphate epimerase (RPE).

The non-naturally occurring microbe may comprise a deletion of a frmRAB operon.

The non-naturally occurring microbe may be derived from a microbe selected from the group consisting of facultative aerobic organisms, facultative anaerobic organisms, and anaerobic organisms. The non-naturally occurring microbe may be derived from a microbe selected from the group consisting of phyla Proteobacteria, Firmicutes, Actinobacteria, Cyanobacteria, Chlorobi, and Deinococcus-Thermus. The non-naturally occurring microbe may be derived from a microbe selected from the group consisting of *Escherichia, Bacillus, Clostridium, Enterobacter, Klebsiella, Enterobacteria, Mannheimia, Pseudomonas, Acinetobacter, Shewanella, Ralstonia, Geobacter, Zymomonas, Acetobacter, Geobacillus, Lactococcus, Streptococcus, Lactobacillus, Corynebacterium, Streptomyces, Propionibacterium, Synechocystis, Synechococcus*, and other *Cyanobacteria, Chlorobi, and Deinococcus*. The non-naturally occurring microbe may be *E. coli*.

The present invention also provides a method for oxidizing methanol. The method comprises growing a non-naturally occurring microbe of the present invention in a medium comprising methanol, whereby the methanol is oxidized. The method may further comprise modifying the heterologous MDH to improve the oxidization of methanol. The method may further comprise fixing $CO_2$. The non-naturally occurring microbe may be grown at a temperature of at least 37° C., at a temperature of at least 30° C., or at a temperature in a range from 30° C. to 37° C. The non-naturally occurring microbe may be grown anaerobically.

The method may further comprise producing a metabolite. The metabolite may be selected from the group consisting of 4-carbon chemicals, diacids, 3-carbon chemicals, higher carboxylic acids, alcohols of higher carboxylic acids, and polyhydroxyalkanoates. The metabolite may be n-butanol. The metabolite may be an amino acid or tricarboxylic acid (TCA) intermediate having a carbon at the fourth position derived from the methanol. The method may further comprise modifying the heterologous MDH to improve the production of the metabolite. Where the microbe expresses one or more heterologous RuMP pathway enzymes, the method may further comprises modifying any one of the one or more heterologous RuMP pathway enzymes to improve the production of the metabolite. The non-naturally occurring microbe may be grown at a temperature of at least 37° C., at a temperature of at least 30° C., or at a temperature in a range from 30° C. to 37° C. The non-naturally occurring microbe may be grown anaerobically.

The present invention further provides a method for making a non-naturally occurring microbe capable of growing in a medium comprising methanol. The preparation method comprises expressing a heterologous methanol dehydrogenase (MDH) in a non-methylotrophic microbe. The MDH is derived from a *Corynebacterium* organism (Cor). The non-methylotrophic microbe comprises a heterologous polynucleotide encoding the MDH. The MDH exhibits a Km of no more than 3 mM for methanol. The methanol may contribute to at least 40% of the carbon source for the non-naturally occurring microbe.

The preparation method may further comprise expressing one or more heterologous ribulose monophosphate (RuMP) pathway enzymes. The one or more heterologous RuMP pathway enzymes may comprise heterologous 3-hexulose-6-phosphate synthase (HPS) and heterologous 3-hexulose-6-phosphate isomerase (PHI).

The preparation method may further comprise expressing one or more heterologous pentose-phosphate pathway (PPP) enzymes in the non-methylotrophic microbe. The one or more heterologous PPP enzymes may comprise heterologous phosphofructokinase (PFK), heterologous fructose bisphosphate aldolase (FBA), heterologous transketolase (TKT), transaldolase (TAL), heterologous fructose/sedoheptulose biphosphatase (GLPX), heterologous ribose-5-phosphate isomerase (RPI), and heterologous ribulose phosphate epimerase (RPE).

DETAILED DESCRIPTION OF THE INVENTION

The present invention relates to engineering *Escherichia coli* (*E. coli*) or other microbes that do not naturally grow on or metabolize methanol to become methylotrophic, that is, capable of using methanol for growth as a sole substrate or co-substrate together with various carbohydrates or other carbon and energy substrates. The resulting non-naturally occurring or recombinant microbes are capable of using the reduction energy from methanol utilization to fix $CO_2$, and produce liquid fuel and chemicals. This technology integrates all critical components required for achieving the overall goal of cost-efficient biofuel production starting from methanol (but ultimately $CH_4$) while at the same time minimizing $CO_2$ release.

Figure 1:
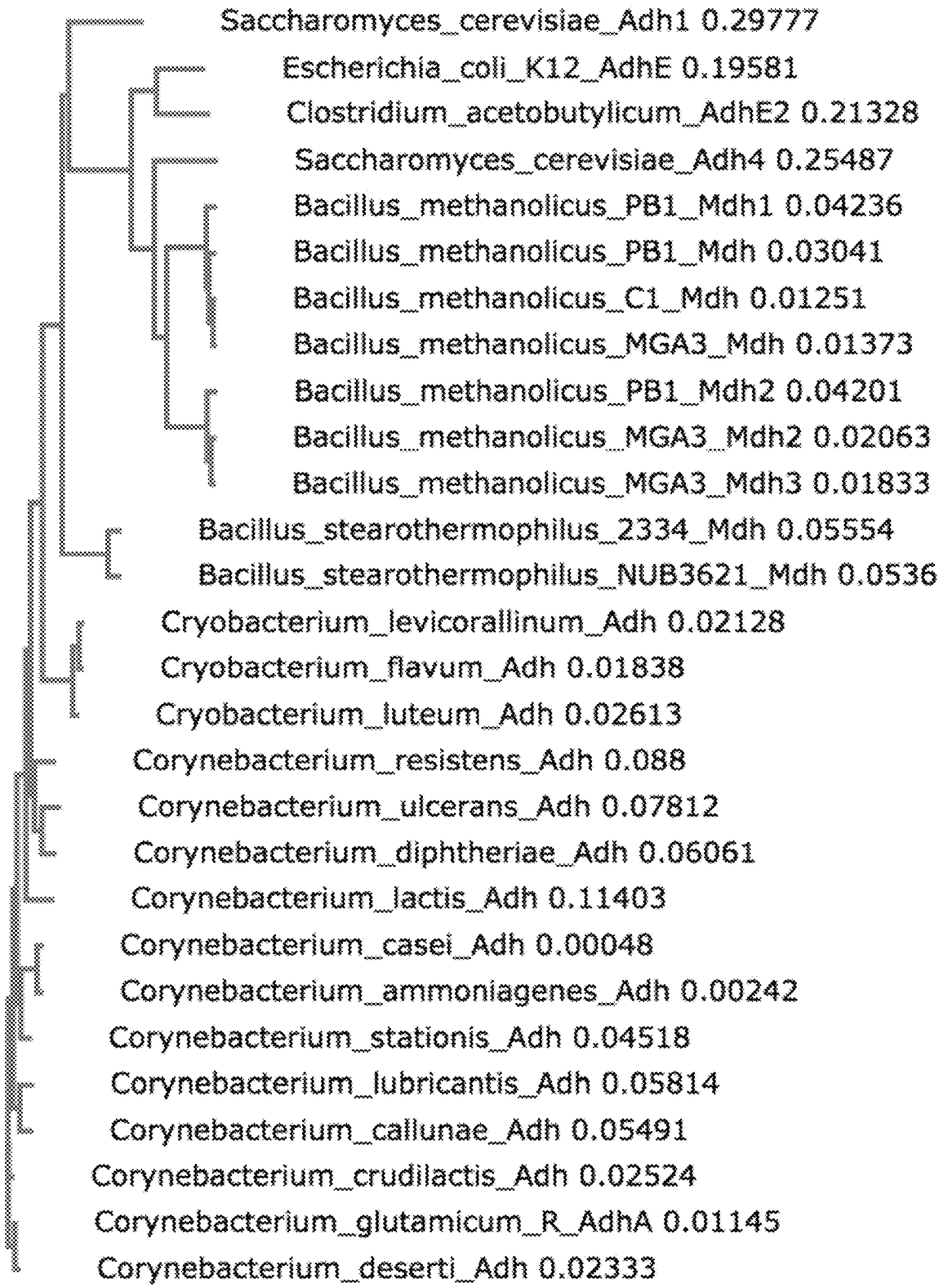
FIG. 1 shows that NAD- and Zn-dependent methanol dehydrogenases (MDHs) belonging to *Corynebacterium* (Cor) organisms, specifically *Corynebacterium glutamicum* (Cgl), are unrelated to the MDHs found in *Bacillus methanolicus* (Bme) and are phylogenetically unique to those found in *Bacillus stearothermophilus* (Bst). Furthermore, MDHs belonging to *Corynebacterium* (Cor) organisms are classified as Group I alcohol dehydrogenases (ADHs) whereas MDHs belonging to *Bacillus methanolicus* (Bme) strains are classified as Group III ADHs. The phylogenetic tree illustrates a Neighbour-joining tree without distance corrections. The analysis involved 28 amino acid sequences. Evolutionary analyses were conducted using Clustal Omega.
Figure 2:
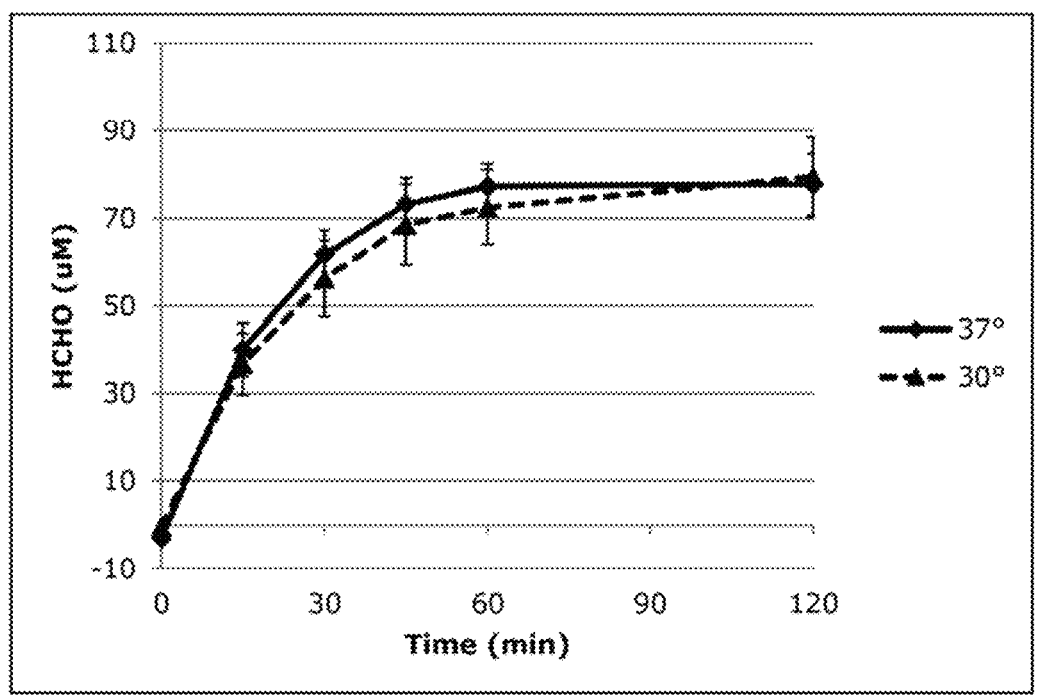
FIG. 2 shows in vivo methanol oxidation activity of *Corynebacterium glutamicum* R (Cgl R) alcohol dehydrogenase A (AdhA) in recombinant *Escherichia coli* cell suspensions. Recombinant *Escherichia coli* cells expressing Cgl AdhA were first grown to a dense concentration in rich media and then resuspended in a minimal media containing 0.5 molar (M) methanol as the only carbon source. Methanol oxidation activity is represented as the formation of formaldehyde (HCHO) over time. Similar in vivo methanol oxidation activities were observed at 30 and 37° C., as indicated.

WO 2015/108777 A1 describes methanol (MeOH) utilization in FIG. 1 and Module 1 in FIG. 2 and $CO_2$ fixation in Module 2 in FIG. 2, which may take place simultaneously to produce various chemicals and fuel molecules, for example, n-butanol (n-BuOH) from acetyl-CoA or pyruvate. The reduction energy contained in MeOH, which is more reduced than certain sugars, e.g., glucose (see reaction 1 of FIG. 2 of WO 2015/108777 A1) may be conserved under anaerobic growth conditions and used to produce various oxygenated molecules such as BuOH and at the same time fix $CO_2$. To achieve this, genes/enzymes for the 3 modules, i.e., MeOH utilization, $CO_2$ fixation, and product formation (e.g., n-BuOH formation) (FIG. 2 of WO 2015/108777 A1), are assembled in a microbe. Each of these goals may be carried out efficiently, and assessed for effectiveness of outcomes by different methods, for example, in terms of rates of MeOH and $CO_2$ utilization, carbon fluxes to pyruvate or acetyl-CoA, and the engineered pathway to produce the desirable product such as n-BuOH (FIG. 2 of WO 2015/108777 A1).

The present invention provides an improved approach to simultaneously use MeOH and $CO_2$, especially under normal growing conditions (e.g., temperature) for microbes such as *E. coli*, to produce n-butanol (n-BuOH) or other chemicals starting with acetyl-CoA, pyruvate, or other intermediate metabolites (or chemicals) of the glycolysis pathway or pentose phosphate pathway, including but not limited to D-xylulose-5-phosphate, D-glyceraldehyde-3-phosphate and/or glycerone. This may be achieved by leveraging genes from methylotrophs for MeOH utilization (Module 1), and various genes from acetogens and other organisms for $CO_2$ fixation (Module 2). Methylotrophic strains may be engineered by combining these two modules with n-BuOH production (Module 3) to produce a chemical or biofuel. Exemplary chemicals include 2, 3, 4, 5 and 6 carbon alcohols, carboxylic acids, ketones, aldehydes and diacids.

Methanol may be used as a carbon source by conversion to formaldehyde (HCHO) by a MeOH dehydrogenase (MDH). HCHO may then be converted to hexulose-6-phosphate, using ribulose-5-phosphate, by a 3-hexulose-6-phosphate synthase (HPS). 3-Hexulose-6-phosphate isomerase (PHI) may convert the hexulose-6-phosphate to fructose-6-phosphate, which may then be used for generation of pyruvate and subsequently acetyl-CoA that may be the starting chemical to feed carbon skeletons into various synthetic pathways to produce various oxychemicals in, for example, the n-BuOH producing pathway (FIG. 2 of WO 2015/108777 A1).

E. coli or the other microbes may be engineered to utilize MeOH as a carbon and energy source by expressing a MeOH dehydrogenase (MDH) and enzymes from the methylotrophic ribulose monophosphate (RuMP) pathway (e.g., HPS and PHI, FIG. 2 of WO 2015/108777). Expression of additional pentose-phosphate pathway (PPP) enzymes as an additional inventive step and strategies including suitable expression promoters may be used to enable or enhance the expression of the corresponding genes in cells when exposed to methanol and/or formaldehyde as substrates.

Significantly, the present invention provides additional steps to make possible the recycling of all or most evolved $CO_2$ from the decarboxylation of pyruvate to acetyl-CoA (FIG. 2 of WO 2015/108777 A1) aiming to minimize $CO_2$ formation. This can be executed for other biological systems independent of MeOH utilization as long as the cells uses a carbon substrate that generates sufficient electrons available for $CO_2$ fixation and also as long as the cells can incorporate formaldehyde into metabolic intermediates. The engineered methylotrophic E. coli or other microbes may be generated for high pathway energy efficiency, yield, and kinetics.

The terms "protein" and "polypeptide" are used herein interchangeably, and refer to a polymer of amino acid residues with no limitation with respect to the minimum length of the polymer. Preferably, the protein or polypeptide has at least 20 amino acids. The definition includes both full-length proteins and fragments thereof, as well as modifications thereof (e.g., glycosylation, phosphorylation, deletions, additions and substitutions). The protein may be an enzyme involved in a biological pathway.

The term "polynucleotide" used herein refers to a polymer of nucleotide residues with no limitation with respect to the minimum length of the polymer. Preferably, the polynucleotide has at least 60 nucleotides. The polynucleotide may be a DNA, cDNA or RNA molecule. A polynucleotide may comprise a gene encoding a desirable protein (e.g., an enzyme), optionally under control of an inducible promoter.

The term "variant" of a protein or polynucleotide used herein refers to a polypeptide having an amino acid or nucleic acid sequence that is the same as the amino acid or nucleic acid sequence of the protein or polynucleotide except having at least one amino acid or nucleic acid modified, for example, deleted, inserted, or replaced, respectively. A variant of a protein or polynucleotide may have an amino acid or nucleic acid sequence at least about 80%, 90%, 95%, or 99%, preferably at least about 90%, more preferably at least about 95%, identical to the corresponding amino acid sequence or nucleic acid of the protein or polynucleotide.

The term "derived from" used herein refers to the origin or source, and may include naturally occurring (i.e., native) and non-naturally occurring (i.e., recombinant) microorganisms or molecules, or variants thereof. For example, a protein derived from a microbe (e.g., a bacterium) may be identical to the corresponding native protein or a variant thereof in the microbe, for example, having an amino acid sequence at least about 70%, 80%, 90%, 95%, or 99% identical to the corresponding native protein. A gene derived from a microbe (e.g., a bacterium) may be identical to the corresponding native gene or a variant thereof in the microbe, for example, having a nucleic acid sequence at least about 80%, 90%, 95%, or 99% identical to the corresponding native gene.

The term "Km" of an enzyme for a substrate refers to the substrate concentration that permits the enzyme to achieve half of the maximum velocity (V max) of an enzymatic reaction on the substrate by the enzyme. The Km value of an enzyme may vary depending on the nature of the substrate or the temperature of the enzymatic reaction.

The present invention provides a non-naturally occurring (i.e., recombinant or synthetic) microbe capable of growing in a medium comprising methanol. The microbe comprises a heterologous polynucleotide that encodes a heterologous methanol dehydrogenase (MDH), which is derived from a Corynebacterium organism (Cor). The MDH is expressed in the microbe. The MDH exhibits a low Km for methanol.

The methanol in the medium may contribute to a significant percentage of the carbon source for the non-naturally occurring microbe. The term "a significant percentage of the carbon source" used herein refers to that the methanol contributes to at least about 40%, 48%, 50%, 60%, 66%, 70%, 80%, 90%, 95%, 99%, or 100% of the carbon source for the non-naturally occurring microbe. Preferably, the methanol may contribute to at least about 40% of the carbon source. Methanol could be also the sole carbon source, i.e., contributing 100% of the carbon source, for the non-naturally occurring microbe. The medium may comprise methanol at a low concentration (e.g., 500, 60 or 20 mM).

The term "microbe" used herein refers to a single cell organism. Examples of microbes include bacteria, archaea, and fungi.

The non-naturally occurring microbe of the present invention may be derived from a microbe selected from the group consisting of facultative aerobic organisms, facultative anaerobic organisms, and anaerobic organisms. In particular, the non-naturally occurring microbe may be derived from a microbe in phyla Proteobacteria, Firmicutes, Actinobacteria, Cyanobacteria, Chloribi, and Deinococcus-Thermus. For example, the non-naturally occurring microbe may be derived from *Escherichia, Bacillus, Clostridium, Enterobacter, Klebsiella, Enterobacteria, Mannheimia, Pseudomonas, Acinetobacter, Shewanella, Ralstonia, Geobacter, Zymomonas, Acetobacter, Geobacillus, Lactococcus, Streptococcus, Lactobacillus, Corynebacterium, Streptomyces, Propionibacterium, Synechocystis, Synechococcus*, and other *Cyanobacteria, Chlorobi, or Deinococcus*. Preferably, the non-naturally occurring microbe of the present invention is E. coli.

The term "methylotrophic microbe" or "methylotroph" used herein refers to a microbe capable of utilizing reduced one carbon compounds, such as methane and methanol, as sole growth and energy sources.

The term "non-methylotrophic microbe" or "non-methylotroph" used herein refers to a microbe incapable of utilizing reduced one carbon compounds, such as methane and methanol, as sole growth and energy sources.

The heterologous methanol dehydrogenase (MDH) is an enzyme capable of converting methanol to formaldehyde (HCHO). The MDH of the present invention is derived from a *Corynebacterium* organism (Cor) and is also referred to herein as Cor MDH. Cor MDHs provide for a better, more effective non-naturally occurring methylotroph. The Cor MDH may exhibit a Km of no more than 3, 1 or 0.1 mM for methanol at, for example, a temperature in a range from about 30° C. to about 37° C., preferably at about 30° C. The Cor MDH may exhibit a Km of at least 30, 35, 50 or 100 mM for butanol at, for example, a temperature in a range from about 30° C. to about 37° C., preferably at about 30° C.

The Cor may be selected from the group consisting of *Corynebacterium glutamicum, Corynebacterium* sp., *Corynebacterium crudilactis, Corynebacterium deserti, Corynebacterium lubricantis, Corynebacterium callunae, Corynebacterium stationis, Corynebacterium casei, Corynebacterium ammoniagenes, Corynebacterium amycolatum, Corynebacterium* sp. HMSC064E07, *Corynebacterium lactis, Corynebacterium* sp. HMSC077G07, *Corynebacterium* sp. HMSC074C05, *Corynebacterium humireducens, Corynebacterium resistens, Corynebacterium vitaeruminis, Corynebacterium durum, Corynebacterium ulcerans, Corynebacterium ulcerans* FRC11, *Corynebacterium ulcerans* NCTC 12077, *Corynebacterium ulcerans* FRC58, *Corynebacterium efficiens, Corynebacterium ulcerans* 0102, *Corynebacterium terpenotabidum, Corynebacterium lipophiloflavum, Corynebacterium diphtheria, Corynebacterium* sp. HMSC034A01, *Corynebacterium* sp. HMSC034B08, *Corynebacterium* sp. HMSC05H05, *Corynebacterium mustelae, Corynebacterium* sp. HMSC04H06, *Corynebacterium pseudotuberculosis, Corynebacterium* sp. HMSC070H05, *Corynebacterium* sp. HMSC29G08, *Corynebacterium* sp. HMSC11D10, *Corynebacterium kutscheri, Corynebacterium freiburgense, Corynebacterium pseudotuberculosis* FRC41, *Corynebacterium* sp. HMSC067D03, *Corynebacterium* sp. HMSC036E10, *Corynebacterium jeddahense, Corynebacterium ciconiae, Corynebacterium coyleae, Corynebacterium sputi, Corynebacterium tuscaniense, Corynebacterium* sp. HMSC074A01, *Corynebacterium variabile, Corynebacterium nuruki, Corynebacterium testudinoris, Corynebacterium striatum, Corynebacterium pseudodiphtheriticum, Corynebacterium* sp. EPI-003-04-2554_SCH2473622, *Corynebacterium* sp. HMSC06C06, *Corynebacterium* sp. SN15, *Corynebacterium propinquum, Corynebacterium* sp. KPL1818, *Corynebacterium* sp. KPL1824, *Corynebacterium timonense, Corynebacterium* sp. KPL1824, *Oyobacterium flavum, Oyobacterium luteum, Cryobacterium levicorallinum, Arthrobacter* sp. 162MFSha1.1, *Rothia* sp. ND6WE1A, and *Arthrobacter* sp. Soil761. For example, the Cor may be *Corynebacterium glutamicum* (Cgl), *Corynebacterium lubricantis* (*C. lubricantis*), *Corynebacterium casei* (*C. casei*) or *Corynebacterium lactis* (*C. lactis*).

In one embodiment, the Cor MDH is alcohol dehydrogenase A (AdhA) of Cgl R (CgAdhA) (GenBank Accession No. BAF55711.1) having the following amino acid sequence (SEQ ID NO: 1):

```
MTTAAPQEFTAAVVEKFGHEVTVKDIDLPKPGPNQALVKVLTSGICHTDL

HALEGDWPVKPEPPFVPGHEGVGEVVELGPGEHDVKVGDIVGNAWLWSAC

GTCEYCITGRETQCNEAEYGGYTQNGSFGQYMLVDTRYAARIPDGVDYLE

AAPILCAGVTVYKALKVSETRPGQFMVISGVGGLGHIAVQYAAAMGMRVI

AVDIADDKLELARKHGAEFTVNARNEDPGEAVQKYTNGGAHGVLVTAVHE
```

-continued
```
AAFGQALDMARRAGTIVFNGLPPGEFPASVFNIVFKGLTIRGSLVGTRQD

LAEALDFFARGLIKPTVSECSLDEVNDVLDRMRNGKIDGRVAIRY.
```

In another embodiment, the Cor MDH comprises an amino acid sequence at least about 70, 80, 90, 95 or 99% identical to SEQ ID NO: 1.

The expression of the heterologous MDH may be under control of a constitutive or an inducible promoter, for example, a formaldehyde responsive promoter, a methanol inducible promoter, a lactose inducible promoter, or a temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically.

The non-naturally occurring microbe of the present invention may further express one or more heterologous ribulose monophosphate (RuMP) pathway enzymes. The term "ribulose monophosphate (RuMP) pathway" as used herein refers to a formaldehyde assimilation pathway in a microbe, which fixes formaldehyde produced via methanol oxidation to the central metabolite ribulose-5-phosphate. Exemplary RuMP pathway enzymes include 3-hexulose-6-phosphate synthase (HPS), and 3-hexulose-6-phosphate isomerase (PHI). The heterologous RuMP pathway enzymes may be derived from any microbe, for example, *M. gastri, B. brevis, B. subtilis, B. methanolicus, Methylobacillus flagellatus,* or *Methylomonas* str. L3, or other obligate or facultative aerobic or anaerobic methylotrophs. Preferably, the RuMP pathway enzymes may be derived from the same microbe. The RuMP pathway enzymes may be expressed as a fusion protein. For example, the heterologous HPS and the heterologous PHI may be expressed as a fusion protein. The expression of any one of the heterologous RuMP pathway enzymes may be under control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous Cor MDH, heterologous HPS, and heterologous PHI.

The non-naturally occurring microbe of the present invention may further express one or more heterologous pentose-phosphate pathway (PPP) enzymes. The term "pentose-phosphate pathway (PPP)" as used herein refers to a cyclic metabolic pathway which functions to regenerate the ribulose-5-phosphate used by the RuMP pathway. Exemplary PPP enzymes include phosphofructokinase (PFK), fructose bisphosphate aldolase (FBA), transketolase (TKT), fructose/sedoheptulose biphosphatase (GLPX), ribulose phosphate epimerase (RPE), ribose-5-phosphate isomerase (RPI) and transaldolase (TAL). The heterologous PPP enzymes (e.g., PFK, FBA, TKT, GLPX, RPE, RPI, and TAL) may be derived from any microbe, for example, any bacterium, archaeon, fungus or even animal cells as long as the genes have been optimized for expression in the host organism as is now well practiced by those skilled in the art. Preferably, the heterologous PPP enzymes are derived from the same microbe. Some or all of the PPP pathway enzymes may be expressed as a fusion protein. The expression of any one of the heterologous PPP enzymes may be under control of a constitutive or an inducible promoter, for example, a formaldehyde or methanol responsive promoter, a lactose inducible promoter, or a temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous Cor MDH, heterologous HPS, heterologous PHI, heterologous PFK, heterologous FBA, heterologous TKT, heterologous GLPX, heterologous TAL, heterologous RPI, and heterologous RPE.

The non-naturally occurring microbe of the present invention may further comprise a deletion of the frmRAB operon.

The non-naturally occurring microbe of the present invention may further express heterologous cyclic formaldehyde dissimilation enzymes. Exemplary cyclic formaldehyde dissimilation enzymes include glucose-6-phosphate isomerase (PGI), glucose-6-phosphate-1-dehydrogenase (ZWF), 6-phosphogluconolactonase (PGL), and 6-phosphogluconate dehydrogenase (GND). The non-naturally occurring microbe of the present invention may contain a deletion of the phosphogluconate dehydratase gene (EDD). The heterologous cyclic formaldehyde dissimilation enzymes may be derived from any microbe. Some or all of the cyclic formaldehyde dissimilation enzymes may be expressed as a fusion protein. The expression of any one of the heterologous cyclic formaldehyde dissimilation enzymes may be under control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous Cor MDH, heterologous HPS, heterologous PHI, heterologous PFK, heterologous FBA, heterologous TKT, heterologous GLPX, heterologous TAL, heterologous RPI, heterologous RPE, heterologous PGI, heterologous ZWF, heterologous PGL, and heterologous GND.

The non-naturally occurring microbe of the present invention may further express heterologous $CO_2$ fixation pathway enzymes. The term "$CO_2$ fixation pathway" as used herein refers to the ability of a microbe to utilize CO2 or it salts such as various mono and bicarbonate salts. Exemplary $CO_2$ fixation pathway enzymes include carbonic anhydrase (CA), formate dehydrogenase (FDH), formaldehyde dehydrogenase (FLD); the enzymes of the reductive tricarboxylic acid cycle such as ATP citrate lyase (ACL), 2-oxoglutarate: ferredoxin oxidoreductase (OGOR), isocitrate dehydrogenase (ICDH), and fumarate reductase (FR); the enzymes of the glycine cleavage system such as aminomethyltransferase (AMT), dehydrolipoyl dehydrogenase (LPDH), glycine dehydrogenase (GDH); and the enzymes of the non-oxidative glycolysis pathway including fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase.

The heterologous $CO_2$ fixation pathway enzymes such as carbonic anhydrase (CA) (EC 4.2.1.1), formate dehydrogenase (FDH) (EC 1.2.1.43 or EC1.2.1.2) and formaldehyde dehydrogenase (FLD) (EC 1.1.1.284) may be derived from several microbes (or host cells), for example, E. coli, acetogenic bacteria, various yeasts or even animal cells. Some or all of the heterologous $CO_2$ fixation pathway enzymes may be expressed as a fusion protein. The expression of any one of the heterologous $CO_2$ fixation pathway enzymes may be under control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. In some preferred embodiments, the non-naturally occurring microbe expresses heterologous Cor MDH, heterologous HPS, heterologous PHI, heterologous PFK, heterologous FBA, heterologous TKT, heterologous GLPX, heterologous RPE, heterologous RPI, heterologous TAL, heterologous PGI, heterologous ZWF, heterologous PGL, heterologous GND, heterologous CA, heterologous FDH, and heterologous FLD.

The non-naturally occurring microbe of the present invention may further express heterologous dihydroxyacetone synthase (DHAS, EC=2.2.1.3), which is also known as formaldehyde transketolase or glycerone synthase. Additionally, the non-naturally occurring microbe may further express heterologous dihydroxyacetone kinase (DAK, EC=2.7.1.29), which is also known as glycerone kinase. The DHAS and DAK may be derived from any microbe, for example, any methylotrophic yeast or from the bacterium Mycobacterium sp. JC1. The expression of any one of the heterologous DHAS and heterologous DAK enzymes may be under control of a constitutive or an inducible promoter, for example, a formaldehyde responsive promoter, a lactose inducible promoter, or temperature sensitive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically In some preferred embodiments, the non-naturally occurring microbe expresses heterologous Cor MDH, heterologous HPS, heterologous PHI, heterologous PFK, heterologous FBA, heterologous TKT, heterologous GLPX, heterologous TAL, heterologous RPI, heterologous RPE, heterologous PGI, heterologous ZWF, heterologous PGL, heterologous GND heterologous CA, heterologous FDH, heterologous FLD, heterologous DHAS, and heterologous DAK.

The present invention provides a method for oxidizing methanol. The method comprises growing a non-naturally occurring microbe of the present invention in a medium comprising methanol.

The present invention also provides a method for producing a metabolite. The method comprises growing a non-naturally occurring microbe of the present invention in a medium comprising methanol.

According to the method for oxidizing methanol or the method for producing a metabolite, the non-naturally occurring microbe may be grown at a temperature of at least about 30° C. or about 37° C. In one embodiment, the non-naturally occurring microbe may be grown at a temperature in a range of about 30° C. to about 37° C. In another embodiment, the non-naturally occurring microbe may be grown at a temperature of about 30° C. In yet another embodiment, the non-naturally occurring microbe may be grown at a temperature of about 37° C.

According to the method for oxidizing methanol or the method for producing a metabolite, the methanol may contribute to a significant percentage of the carbon source for the non-naturally occurring microbe. The methanol may contribute to at least about 40%, 48%, 50%, 60%, 66%, 70%, 80%, 90%, 95%, 99%, or 100% of the carbon source for the non-naturally occurring microbe. Preferably, the methanol may contribute to at least about 40% of the carbon source. More preferably, the methanol is the sole carbon source, i.e., contributing 100% of the carbon source, for non-naturally occurring microbe.

According to the method for oxidizing methanol or the method for producing a metabolite, the medium may further comprise other carbon source, for example, fermentable mono, di, oligo or polysaccharides. Exemplary fermentable monosaccharides include glucose, xylose, mannose, arabinose, rhamnose, and ribose. Fermentable di- or oligosaccharides may be sucrose, lactose, maltose, cellobiose, short polymers of these mono- or di-saccharides, or long polymers of saccharides, for example, cellulose and xylan. The other carbon source may contribute to no more than about 40%, preferably no more than about 30%, more preferably no more than about 20%, most preferably no more than about 10% of the carbon source for the non-naturally occurring microbe.

The metabolite may be selected from the group consisting of 4-carbon chemicals, diacids, 3-carbon chemicals, higher carboxylic acids, alcohols of higher carboxylic acids, polyhydroxyalkanoates, and specialty chemicals. The 4-carbon chemicals may be selected from the group consisting of butyrate, n-butanol, i-butanol, 2-butanol, 2,3-butanediol, and 1,4-butanediol. The diacids may be selected from the group consisting of oxalic, malonic, succinic, glutaric, adipic, pimelic, pthalic, isopthalic, and terephtlalic. The 3-carbon chemicals may be selected from the group consisting of propanol, propanediol, lactate, and acrylate. The higher carboxylic acids may be selected from the group consisting of pentanoic acids and hexanoic acids. Preferably, the metabolite is n-butanol. The specialty chemicals may include artemisinin, vanillin, anthocyanins, resveratrol, et cetera.

According to the method for producing a metabolite, at least about 30%, 40%, 50%, 60%, 70%, 80%, 90% or 100%, preferably at least about 80%, of the carbon in the metabolite is derived from the methanol. In some embodiments, the metabolite is an amino acid or tricarboxylic acid (TCA) intermediate having at one or multiple carbon positions of the chemical up to the fourth position derived from the methanol. The present method may produce a desirable metabolite at about 50-100 mg.

The growing conditions for the non-naturally occurring microbe may be modified to improve the metabolite production, methanol oxidization or methanol utilization. For example, the non-naturally occurring microbe may be grown anaerobically, or at a temperature of at least about 30° C. or 37° C., for example, at about 30° C., 37° C., 40° C., 45° C. or 50° C., or in a range from about 30° C. to about 37° C.

A gene encoding a heterologous enzyme, for example, MDH, the RuMP pathway enzymes (e.g., HPS and PHI), the PPP pathway enzymes (e.g., PFK, FBA, TKT, TAL, GLPX, RPI, and RPE), the cyclic formaldehyde dissimilation enzymes (e.g., PGI, ZWF, PGL, and GND), the $CO_2$ fixation pathway enzymes (e.g., CA, FDH, FLD, reductive tricarboxylic acid cycle enzymes such as ACL, OGOR, ICDH, and FR, glycine cleavage system enzymes such as AMT, LPDH, GDH, non-oxidative glycolysis pathway enzymes such as fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase, DHAS, and DAK, may be modified to improve metabolite production, methanol oxidization or methanol utilization. The gene may be engineered to be under control of an inducible promoter, for example, a formaldehyde or methanol responsive promoter, a lactose inducible promoter, or a temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. The gene may also be engineered to modify the corresponding enzyme (e.g., MDH) to improve the enzyme's substrate specificity and optimal temperature in the non-naturally occurring microbe.

The method for producing a metabolite may further comprise fixing $CO_2$. The medium may be modified by containing higher levels of methanol which is more reduced than a sugar (e.g., glucose) such that more electrons may be generated under the conditions the non-naturally occurring microbe is grown. Other media modifications may also enable an enhanced availability of electrons in the cells. Such additives would be reducing agents or dyes (such as Methyl Viologen (MV) and other viologens). Such electrons may enable the non-naturally occurring microbe to grow on the medium while fixing $CO_2$. According to this method, $CO_2$ release may be reduced by at least about 20%, preferably by at least about 30-50%, more preferably up to about 75%.

A method for making a non-naturally occurring microbe capable of growing in a medium comprising methanol is provided. The preparation method comprises expressing a heterologous methanol dehydrogenase (MDH) in a non-methylotrophic microbe. The MDH is derived from a *Corynebacterium* organism (Cor). The non-methylotrophic microbe comprises a heterologous polynucleotide encoding the MDH. The MDH exhibits a low Km for methanol, for example, no more than about 3, 1 or 0.1 mM at, for example, a temperature in a range from about 30° C. to about 37° C., preferably at about 30° C. The methanol may contribute to a significant percentage (e.g., at least about 40%, 48%, 50%, 60%, 66%, 70%, 80%, 90%, 95%, 99%, or 100%) of the carbon source for the non-naturally occurring microbe.

The preparation method may further comprise expressing one or more heterologous ribulose monophosphate (RuMP) pathway enzymes in the non-methylotrophic microbe. The RuMP pathway enzymes may include 3-hexulose-6-phosphate synthase (HPS), 3-hexulose-6-phosphate isomerase (PHI).

The preparation method may further comprise expressing one or more heterologous pentose-phosphate pathway (PPP) enzymes in the non-methylotrophic microbe. The PPP enzymes may include phosphofructokinase (PFK), fructose bisphosphate aldolase (FBA), transketolase (TKT), transaldolase (TAL) fructose/sedoheptulose biphosphatase (GLPX), ribulose phosphate epimerase (RPE), and ribose-5-phosate isomerase (RPI).

The preparation method may further comprise expressing one or more heterologous cyclic formaldehyde dissimilation enzymes in the non-methylotrophic microbe. The enzymes may include glucose-6-phosphate isomerase (PGI), glucose-6-phosphate-1-dehydrogenase (ZWF), 6-phosphogluconolactonase (PGL), and 6-phosphogluconate dehydrogenase (GND). The non-naturally occurring microbe of the present invention may contain a deletion of the phosphogluconate dehydratase gene (EDD).

The preparation method may further comprise expressing one or more heterologous $CO_2$ fixation pathway enzymes in the non-methylotrophic microbe. The heterologous $CO_2$ fixation pathway enzymes may include carbonic anhydrase (CA), formate dehydrogenase (FDH), formaldehyde dehydrogenase (FLD; the enzymes of the reductive tricarboxylic acid cycle such as ATP citrate lyase (ACL), 2-oxoglutarate: ferredoxin oxidoreductase (OGOR), isocitrate dehydrogenase (ICDH), and fumarate reductase (FR); the enzymes of the glycine cleavage system such as aminomethyltransferase (AMT), dehydrolipoyl dehydrogenase (LPDH), glycine dehydrogenase (GDH); and the enzymes of the non-oxidative glycolysis pathway including fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase.

The preparation method may further comprise expressing one or more heterologous dihydroxyacetone synthase (DHAS, EC=2.2.1.3) in the non-methylotrophic microbe. DHAS is also known as formaldehyde transketolase or glycerone synthase. The non-methylotrophic microbe may further express heterologous dihydroxyacetone kinase (DAK, EC=2.7.1.29). DAK is also known as glycerone kinase.

The preparation method may further comprise introducing into the non-methylotrophic microbe a gene encoding any of the heterologous enzymes selected from the group consisting of the heterologous MDH, the heterologous RuMP pathway enzymes (e.g., HPS and PHI), the heterologous PPP enzymes (e.g., PFK, FBA, TKT, GLPX, TAL, RPI and RPE), the heterologous cyclic formaldehyde dissimilation pathway (PGI, ZWF, PGL, GND), the heterologous $CO_2$ fixation pathway enzymes (e.g., CA, FDH, FLD, reductive tricarboxylic acid cycle enzymes such as ACL, OGOR, ICDH, and FR, glycine cleavage system enzymes such as AMT, LPDH, GDH, non-oxidative glycolysis pathway enzymes such as fructose phosphoketolase, xylose phosphoketolase, transaldolase, transketolase, fructose 1,2-bisphosphate aldolase, fructose 1,6-bisphosphatase, ribulose-5-phosphate epimerase, ribose-5-phosphate isomerase, and trios phosphate isomerase), heterologous DHAS, and heterologous DAK. The gene may be expressed transiently in the non-methylotrophic microbe. The gene may be integrated into the genome of the non-methylotrophic microbe. The gene may be under control of an inducible promoter, for example, a formaldehyde or methanol responsive promoter, a lactose inducible promoter, or temperature or pH responsive promoter. These promoters may be derived from a host cell (native) or exogenously, for example, the T7 phage promoter. These genes may also be under the control of non-DNA regulatory elements such as small RNA, antisense RNA, sensing RNA, temperature sensitive RNA or any combination thereof. The translation of these genes may be initiated with a range of ribosomal binding sites of varying strength. These genes may be borne on plasmids, fosmids, bacterial artificial chromosomes or be integrated into the host chromosome. These genes may be configured monocistronically or polycistronically. The non-naturally occurring microbe may also contain deletions of the fmrRAB operon and the edd gene.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Cgl-MDH Form a Unique Group of Methanol Dehydrogenases (MDHs) Distinct from Previously Characterized MDHs

*Corynebacterium glutamicum* (Cgl) is a mesophilic Gram positive bacterium that possesses the ability to oxidize, but not assimilate methanol. Blast analysis using the Cgl R AdhA as template revealed the existence of 150 homologues that share at least 60 identity on the amino acid level (Table 1). Phylogenic analysis of these genes revealed that the Cgl-MDH genes are unrelated to the *Bacillus methanolicus* (Bme) MDHs and also form a unique grouping compared with the *Bacillus stearothermophilus* (Bst) MDH genes (FIG. 1).

Example 2. Optimized Methanol Utilization in One or Sequential Bioreactors with Optimized Temperature for Optimal MDH Activity Thermodynamic calculations show a positive change in reduction potential and negative change in reaction Gibbs free energy when calculated using estimated physiological conditions (Table 2). This suggests that MeOH oxidation via NAD-dependent MDH enzymes becomes more favorable at higher temperatures, i.e., the optimal growth temperature of 45-55° C. of these thermophilic *Bacillus methylotrophs*.

Specifically, the change in the reaction Gibbs free energy ($\Delta_r G$) decreases from −1.0 to −2.9 kJ/mol as the temperature increases from 37 to 55° C., suggesting a more favorable reaction at higher temperatures. This further demonstrates that MeOH oxidation via NAD-dependent MDH enzymes is plausible under the physiological growth conditions of mesophiles such as E. coli. As MeOH oxidation via NAD-dependent MDH enzymes is favorable only to a small extent under physiological conditions compared with the other methanol oxidation systems, the immediate consumption of HCHO via an assimilation pathway will increase the favorability of MeOH oxidation. For example, at 37° C., when the concentration of HCHO is lowered from 0.17 to 0.017 mM, the change in the reaction Gibbs free energy decreases from −1.0 to −7.0 kJ/mol while the equilibrium constant shifts from 0.925 to 8.5, thus becoming much more favorable. Therefore, increased methanol oxidation within synthetic methylotrophic organisms may be achieved by keeping the intracellular HCHO concentration at very low levels, likely through its immediate consumption via a HCHO assimilation pathway.

Importantly, the aforementioned and cloned Cgl-family MDHs, are sourced from organisms that are natively mesophilic and are typically cultivated at 30° C. As demonstrated in FIG. 2, the in vivo methanol oxidation is unaffected by temperature and can be observed as low as 30° C. These data support the hypothesis that Cgl-MDH can act as superior methanol dehydrogenases as they appear to not be as dependent on elevated fermentation temperatures to function.

Figure 3:
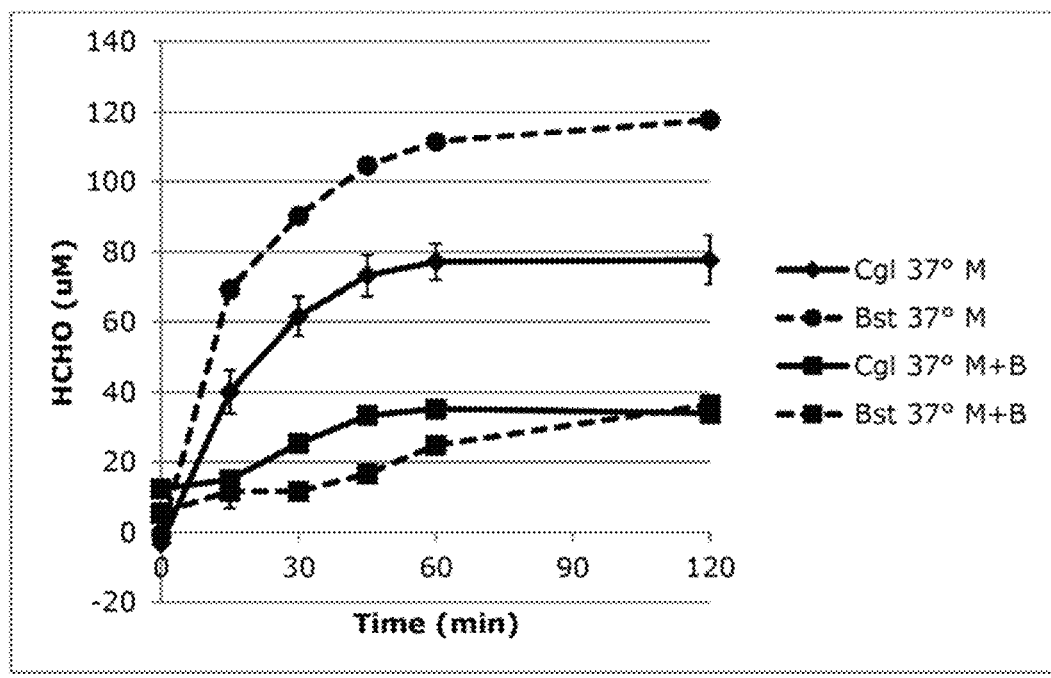
FIG. 3 shows in vivo alcohol selectivity of *Corynebacterium glutamicum* R (Cgl R) alcohol dehydrogenase A (AdhA) and *Bacillus stearothermophilus* 2334 (Bst) methanol dehydrogenase (Mdh) in recombinant *Escherichia coli* cell suspensions. Recombinant *Escherichia coli* cells expressing either Cgl AdhA or Bst Mdh were first grown to a dense concentration in rich media and then resuspended in a minimal media containing 0.5 molar methanol (M) as the only carbon source or 0.5 molar methanol and 0.05 molar n-butanol (B) as the only carbon sources. Methanol oxidation activity is represented as the formation of formaldehyde (HCHO) over time. As illustrated, Cgl AdhA retains more methanol oxidation activity in the presence of n-butanol compared to Bst Mdh. This makes Cgl AdhA an ideal enzyme candidate for the production of higher alcohols, e.g., n-butanol, in a synthetic methylotrophic organism.
Figure 7:
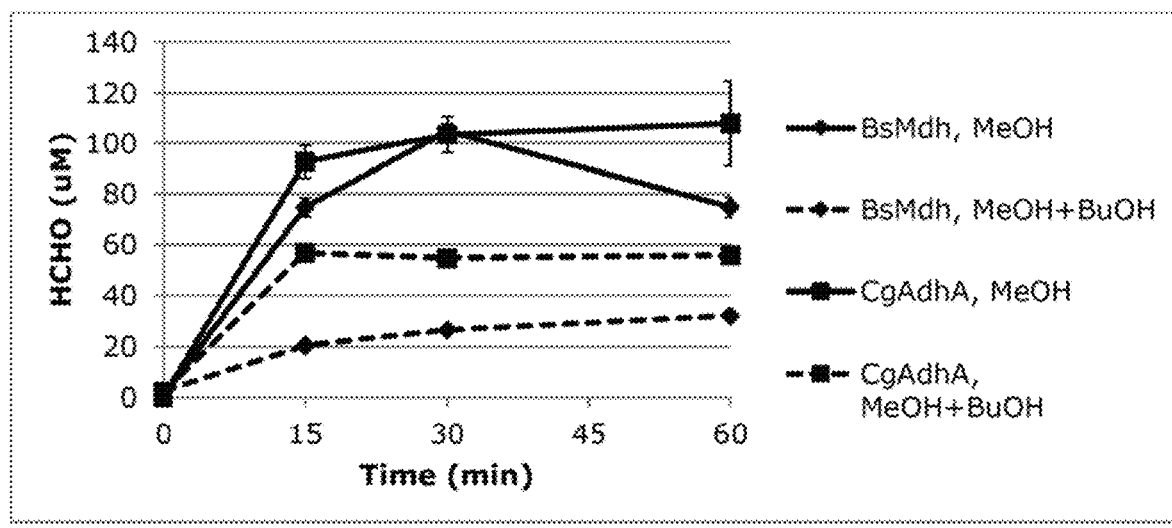
FIG. 7 shows in vivo alcohol selectivity of *Bacillus stearothermophilus* 2334 (Bst) methanol dehydrogenase (BsMdh) and *Corynebacterium glutamicum* R (Cgl R) alcohol dehydrogenase A (AdhA) at intermediate methanol concentrations (60 mM) in recombinant *Escherichia coli* cell suspensions. Recombinant *Escherichia coli* cells expressing either BsMdh or CgAdhA were first grown to a dense concentration in rich media and then resuspended in a minimal media containing 60 millimolar (mM) methanol (MeOH) as the only carbon source or 60 millimolar (mM) methanol (MeOH) and 10 millimolar (mM) n-butanol (BuOH) as the only carbon sources. Methanol oxidation activity is represented as the formation of formaldehyde (HCHO) over time. CgAdhA retains more methanol oxidation activity in the presence of low n-butanol concentrations compared to BsMdh, as indicated. This makes CgAdhA an ideal enzyme candidate for the production of higher alcohols, e.g. n-butanol, in a synthetic methylotrophic organism.
Figure 8:
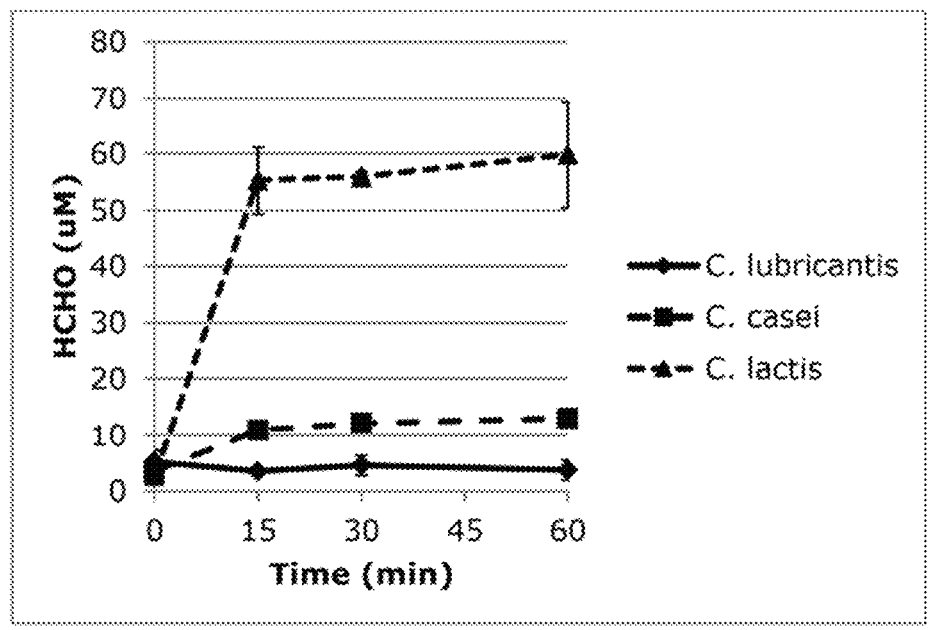
FIG. 8 shows in vivo methanol oxidation activity of alternatively sourced *Corynebacterium* alcohol dehydrogenases (*Corynebacterium lubricantis* alcohol dehydrogenase (*C. lubricantis*), *Corynebacterium casei* alcohol dehydrogenase (*C. casei*) and *Corynebacterium lactis* alcohol dehydrogenase (*C. lactis*)) at intermediate methanol concentrations (60 mM) in recombinant *Escherichia coli* cell suspensions. Recombinant *Escherichia coli* cells expressing either *C. lubricantis*, *C. casei* or *C. lactis* alcohol dehydrogenase were first grown to a dense concentration in rich media and then resuspended in a minimal media containing 60 millimolar (mM) methanol as the only carbon source. Methanol oxidation activity is represented as the formation of formaldehyde (HCHO) over time. *C. lactis* alcohol dehydrogenase exhibited the highest methanol oxidation activity at intermediate methanol concentrations, followed by *C. casei* and finally *C. lubricantis* alcohol dehydrogenases, as indicated. This makes *C. lactis* alcohol dehydrogenase an alternative ideal enzyme candidate for synthetic methylotrophic organisms growing in intermediate methanol concentrations.
Figure 9:
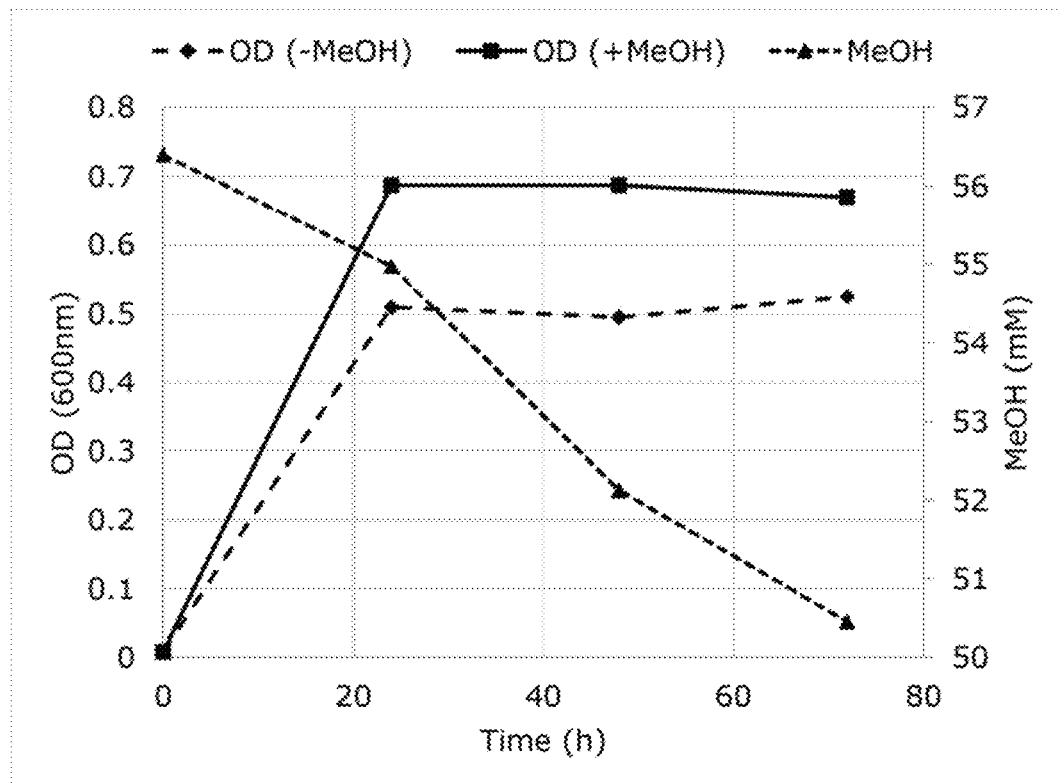
FIG. 9 shows growth dynamics of recombinant *Escherichia coli* expressing *Bacillus stearothermophilus* 2334 (Bst) methanol dehydrogenase (Mdh), *Bacillus methanolicus* MGA3 (Bme) hexulose phosphate synthase (HPS) and *Bacillus methanolicus* MGA3 (Bme) hexulose phosphate isomerase (PHI). All heterologous enzymes were expressed in an operon under the control of a formaldehyde responsive promoter (Pfrm) sourced from the native frmRAB operon in *Escherichia coli*. Recombinant *Escherichia coli* cells harboring a knockout of the native formaldehyde dehydrogenase gene (frmA) were grown in minimal media containing 1 gram per liter of yeast extract and supplemented with methanol as a co-substrate. As illustrated, cultures supplemented with methanol demonstrate higher biomass yields compared with those not supplemented with methanol. This indicates that expression of essential methylotrophic enzymes (MDH, HPS and PHI) are regulated and expressed using a formaldehyde responsive promoter and lead to methanol assimilation in a synthetic methylotrophic organism.
Figure 10:
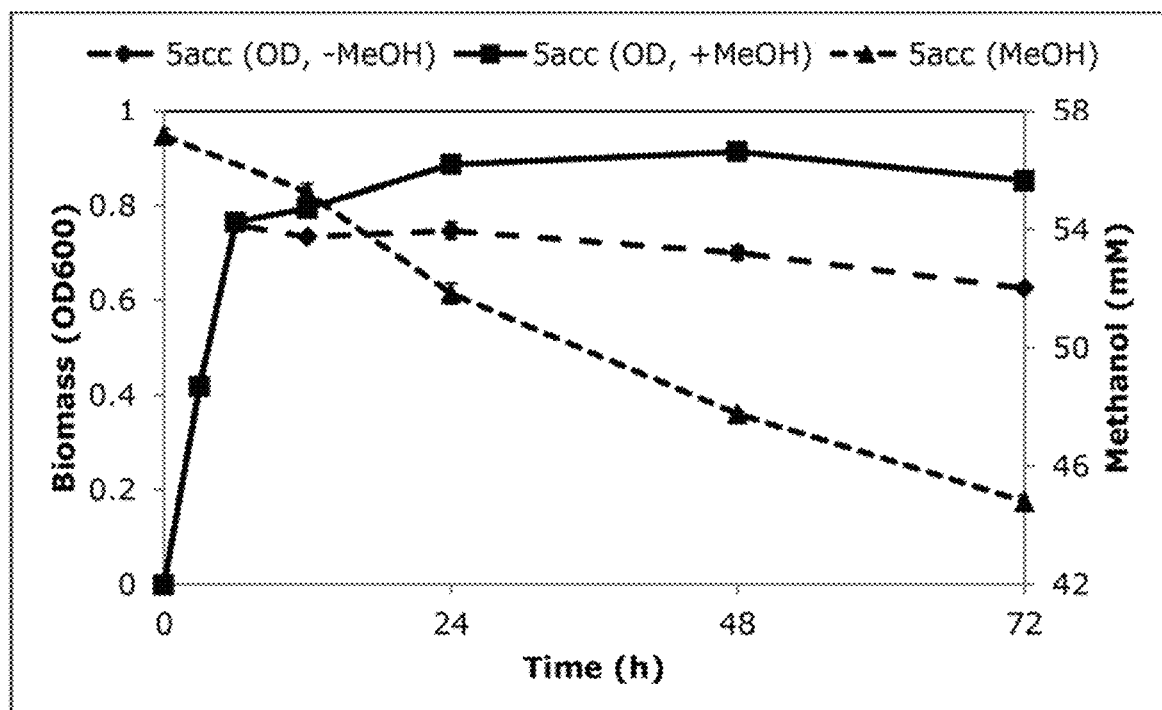
FIG. 10 shows growth dynamics of recombinant *Escherichia coli* expressing *Bacillus stearothermophilus* 2334 (Bst) methanol dehydrogenase (Mdh), *Bacillus methanolicus* MGA3 (Bme) hexulose phosphate synthase (HPS), *Bacillus methanolicus* MGA3 (Bme) hexulose phosphate isomerase (PHI), *Bacillus methanolicus* MGA3 (Bme) ribulose phosphate epimerase (RPE), *Bacillus methanolicus* MGA3 (Bme) fructose bisphosphate aldolase (FBA), *Bacillus methanolicus* MGA3 (Bme) fructose/sedoheptulose aldolase (GLPX), *Bacillus methanolicus* MGA3 (Bme) phosphofructokinase (PFK) and *Bacillus methanolicus* MGA3 (Bme) transketolase (TKT). Recombinant *Escherichia coli* cells harboring a knockout of the native formaldehyde dehydrogenase gene (frmA) were grown in minimal media containing 1 gram per liter of yeast extract and supplemented with methanol as a co-substrate. As illustrated, cultures supplemented with methanol demonstrate higher biomass yields compared with those not supplemented with methanol. This indicates that expression of essential methylotrophic enzymes (MDH, HPS and PHI) and heterologous pentose phosphate pathway (PPP) enzymes (RPE, FBA, GLPX, PFK and TKT) lead to methanol assimilation in a synthetic methylotrophic organism.
Figure 11:
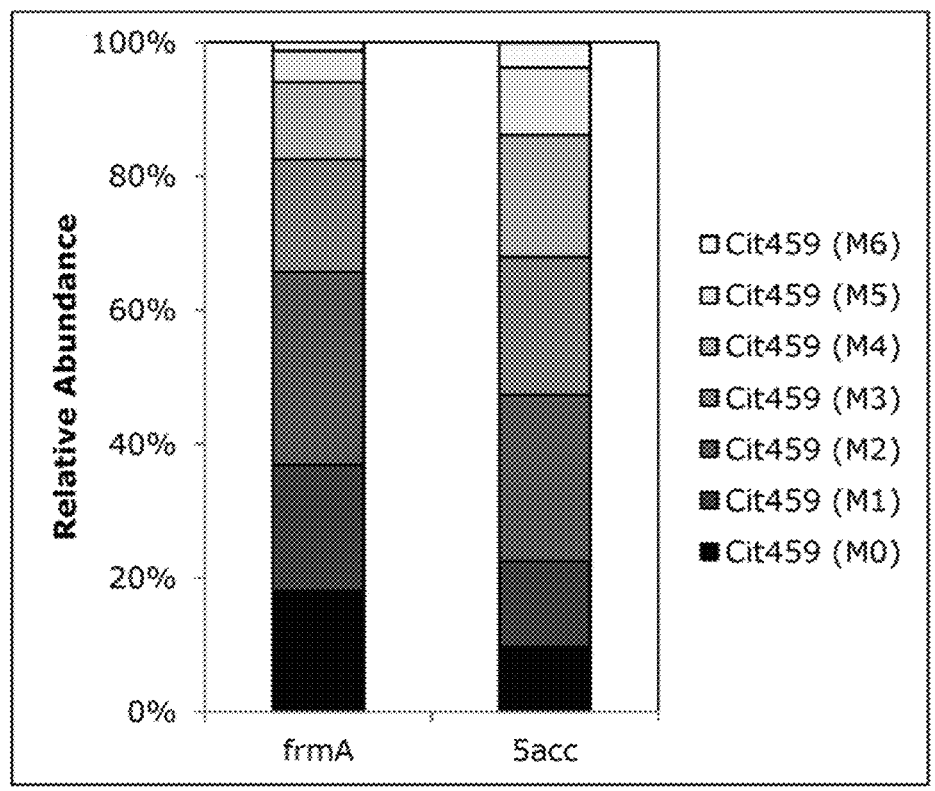
FIG. 11 shows $^{13}$C-methanol mass isotopomer labeling in the TCA cycle intermediate citrate in recombinant *Escherichia coli* expressing either *Bacillus stearothermophilus* 2334 (Bst) methanol dehydrogenase (Mdh), *Bacillus methanolicus* MGA3 (Bme) hexulose phosphate synthase (HPS) and *Bacillus methanolicus* MGA3 (Bme) hexulose phosphate isomerase (PHI) (labeled as frmA) or *Bacillus stearothermophilus* 2334 (Bst) methanol dehydrogenase (Mdh), *Bacillus methanolicus* MGA3 (Bme) hexulose phosphate synthase (HPS), *Bacillus methanolicus* MGA3 (Bme) hexulose phosphate isomerase (PHI), *Bacillus methanolicus* MGA3 (Bme) ribulose phosphate epimerase (RPE), *Bacillus methanolicus* MGA3 (Bme) fructose bisphosphate aldolase (FBA), *Bacillus methanolicus* MGA3 (Bme) fructose/sedoheptulose aldolase (GLPX), *Bacillus methanolicus* MGA3 (Bme) phosphofructokinase (PFK) and *Bacillus methanolicus* MGA3 (Bme) transketolase (TKT) (labeled as 5acc). Recombinant *Escherichia coli* cells harboring a knockout of the native formaldehyde dehydrogenase gene (frmA) were grown in minimal media containing 1 gram per liter of yeast extract and supplemented with $^{13}$C-methanol as a co-substrate. As illustrated, the 5acc *Escherichia coli* strain demonstrated a higher depth of labeling in citrate, a TCA cycle intermediate, compared to the frmA *Escherichia coli* strain. This indicates that the heterologous pentose phosphate pathway (PPP) enzymes from *Bacillus methanolicus* MGA3 (Bme) improve cycling and efficiency of the heterologous ribulose monophosphate (RuMP) pathway in a synthetic methylotrophic organism, e.g. *Escherichia coli*. As illustrated, all possible mass isotopomers from completely unlabeled to completely labeled citrate could be observed, e.g. M6 represents the mass isotopomer containing labeled carbon ($^{13}$C) at all 6 possible positions.

Example 3. Cgl-Family MDH Exhibit Greater Specificity Towards Methanol than Higher Order Alcohols We have performed in vivo MDH activity assays comparing the Cgl MDH with the previously described Bst MDH for substrate specificity. Cells were suspended in minimal media containing either 500 mM MeOH only, or a mixture of 500 mM MeOH and 50 mM n-BuOH. MDH activity was assessed by measuring formaldehyde (HCHO) production over time (FIG. 3). Alternatively, 60 mM MeOH or a mixture of 60 mM MeOH and 10 mM n-BuOH was assessed (FIG. 7). Our results demonstrate that the Cgl MDH is less affected by the presence of butanol than is the Bst MDH, likely due to its much higher Km towards butanol (Table 3). Based on these results, we hypothesize that the Cgl MDH is the superior candidate enzyme to be used in the recombinant E. coli strain for the production of biofuel, since product formation will not have as significant of an impact on methanol oxidation.

Figure 4:
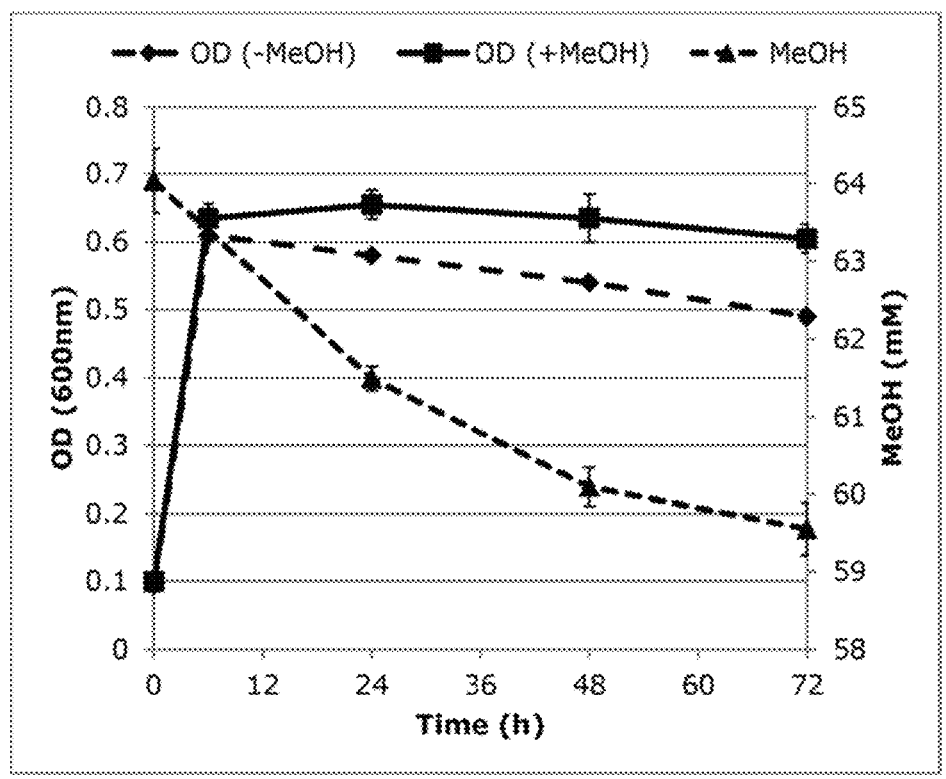
FIG. 4 shows growth dynamics of recombinant *Escherichia coli* expressing *Corynebacterium glutamicum* R (Cgl R) alcohol dehydrogenase A (AdhA), *Bacillus methanolicus* MGA3 (Bme) hexulose phosphate synthase (HPS and *Bacillus methanolicus* MGA3 (Bme) hexulose phosphate isomerase (PHI). Cells were grown in minimal media containing 1 gram per liter of yeast extract and supplemented with methanol as a co-substrate. As illustrated, cultures supplemented with methanol demonstrate higher biomass yields compared with those not supplemented with methanol. This indicates that Cgl AdhA is responsible for the initial methanol oxidation that leads to methanol assimilation in a synthetic methylotrophic organism.
Figure 5:
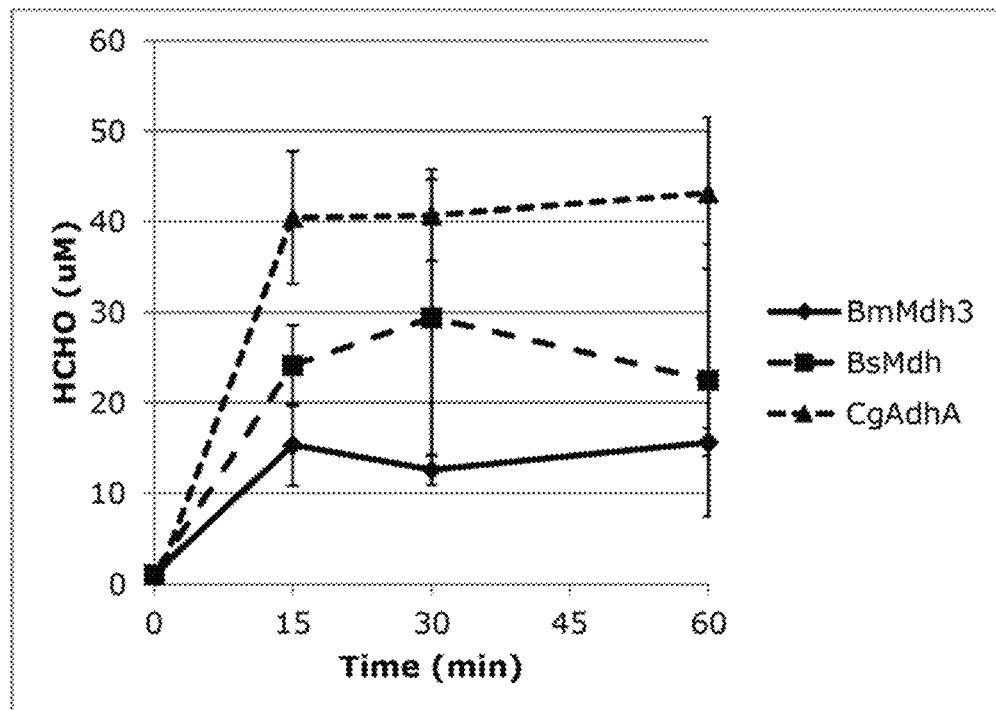
FIG. 5 shows in vivo methanol oxidation activity of *Bacillus methanolicus* MGA3 (Bme) methanol dehydrogenase 3 (BmMdh3), *Bacillus stearothermophilus* 2334 (Bst) methanol dehydrogenase (BsMdh) and *Corynebacterium glutamicum* R (Cgl R) alcohol dehydrogenase A (AdhA) at low methanol concentrations (20 mM) in recombinant *Escherichia coli* cell suspensions. Recombinant *Escherichia coli* cells expressing either BmMdh3, BsMdh or CgAdhA were first grown to a dense concentration in rich media and then resuspended in a minimal media containing 20 millimolar (mM) methanol as the only carbon source. Methanol oxidation activity is represented as the formation of formaldehyde (HCHO) over time. CgAdhA exhibited the highest methanol oxidation activity at low methanol concentrations, followed by BsMdh and finally BmMdh3, as indicated. This makes CgAdhA an ideal enzyme candidate for synthetic methylotrophic organisms growing in low methanol concentrations.
Figure 6:
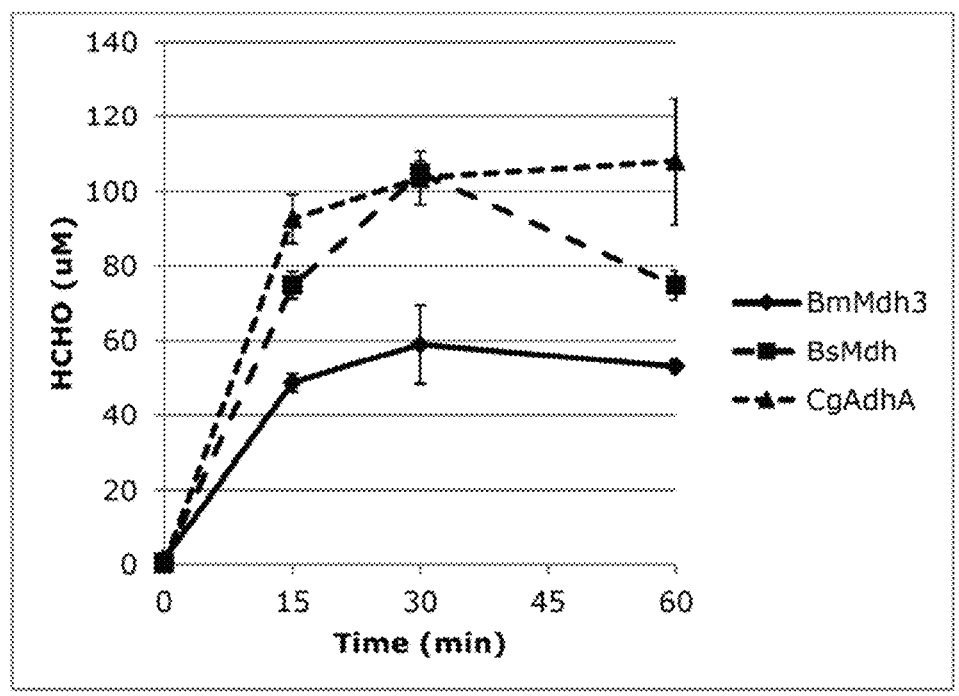
FIG. 6 shows in vivo methanol oxidation activity of *Bacillus methanolicus* MGA3 (Bme) methanol dehydrogenase 3 (BmMdh3), *Bacillus stearothermophilus* 2334 (Bst) methanol dehydrogenase (BsMdh) and *Corynebacterium glutamicum* R (Cgl R) alcohol dehydrogenase A (AdhA) at intermediate methanol concentrations (60 mM) in recombinant *Escherichia coli* cell suspensions. Recombinant *Escherichia coli* cells expressing either BmMdh3, BsMdh or CgAdhA were first grown to a dense concentration in rich media and then resuspended in a minimal media containing 60 millimolar (mM) methanol as the only carbon source. Methanol oxidation activity is represented as the formation of formaldehyde (HCHO) over time. CgAdhA exhibited the highest methanol oxidation activity at intermediate methanol concentrations, followed by BsMdh and finally BmMdh3, as indicated. This makes CgAdhA an ideal enzyme candidate for synthetic methylotrophic organisms growing in intermediate methanol concentrations.

Example 4. Growth on Methanol and Biomass Labeling from $^{13}$C Methanol of an E. coli Strain Carrying Plasmid pETM6PtacCgl_MDH/Bm_RuMP Growth dynamics of recombinant *Escherichia coli* expressing *Corynebacterium glutamicum* R (Cgl R) alcohol dehydrogenase A (AdhA), *Bacillus methanolicus* MGA3 (Bme) hexulose phosphate synthase (HPS) and *Bacillus methanolicus* MGA3 (Bme) hexulose phosphate isomerase (PHI). Cells were grown in minimal media containing 1 gram per liter of yeast extract and supplemented with methanol as a co-substrate. As illustrated in FIG. 4, cultures supplemented with methanol demonstrate higher biomass yields compared with those not supplemented with methanol. This indicates that Cgl AdhA is responsible for the initial methanol oxidation that leads to methanol assimilation in a synthetic methylotrophic organism.

Figure 12:
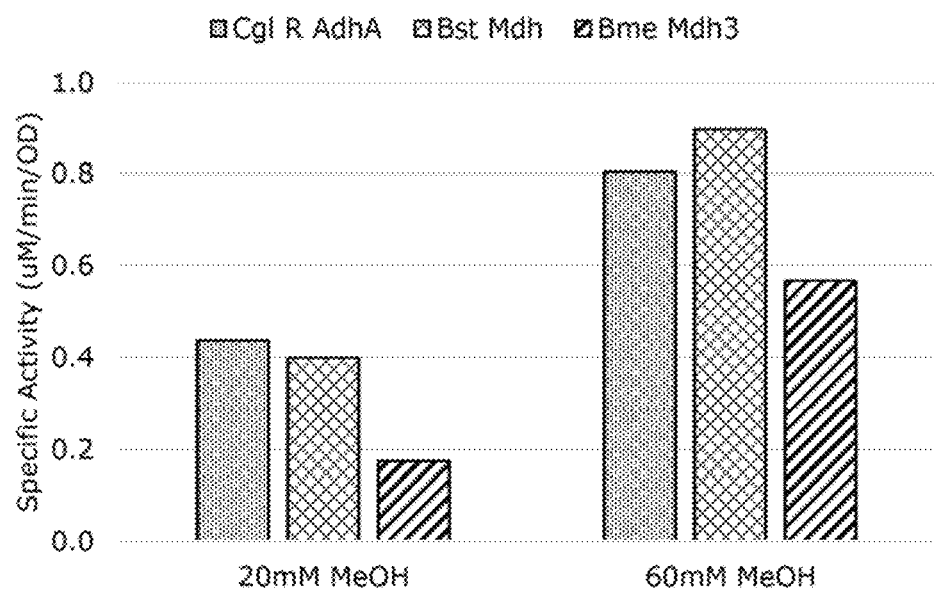
FIG. 12 shows specific activity of in vivo methanol oxidation of *Bacillus methanolicus* MGA3 (Bme) methanol dehydrogenase 3 (Mdh3), *Bacillus stearothermophilus* 2334 (Bst) methanol dehydrogenase (Mdh) and *Corynebacterium glutamicum* R (Cgl R) alcohol dehydrogenase A (AdhA) at various methanol concentrations in recombinant *Escherichia coli* cell suspensions. Recombinant *Escherichia coli* cells expressing either Bme Mdh3, Bst Mdh or Cgl R AdhA were first grown to a dense concentration in rich media and then resuspended in a minimal media containing the indicated methanol concentration as the only carbon source. Specific activity of methanol oxidation was calculated as the slope of initial formaldehyde (HCHO) formation normalized to biomass concentration. Cgl R AdhA and Bst Mdh exhibited higher specific activities than did Bme Mdh3 at both methanol concentrations, as indicated. This suggests that both Cgl R AdhA and Bst Mdh possess lower Km values for methanol, as indicated by higher activity at lower methanol concentrations. Furthermore, Cgl R AdhA exhibits a higher specific activity at the lowest methanol concentration, suggesting that it possesses a lower Km for methanol than does Bst Mdh, which has been verified in the literature though in vitro characterization.
Figure 13:
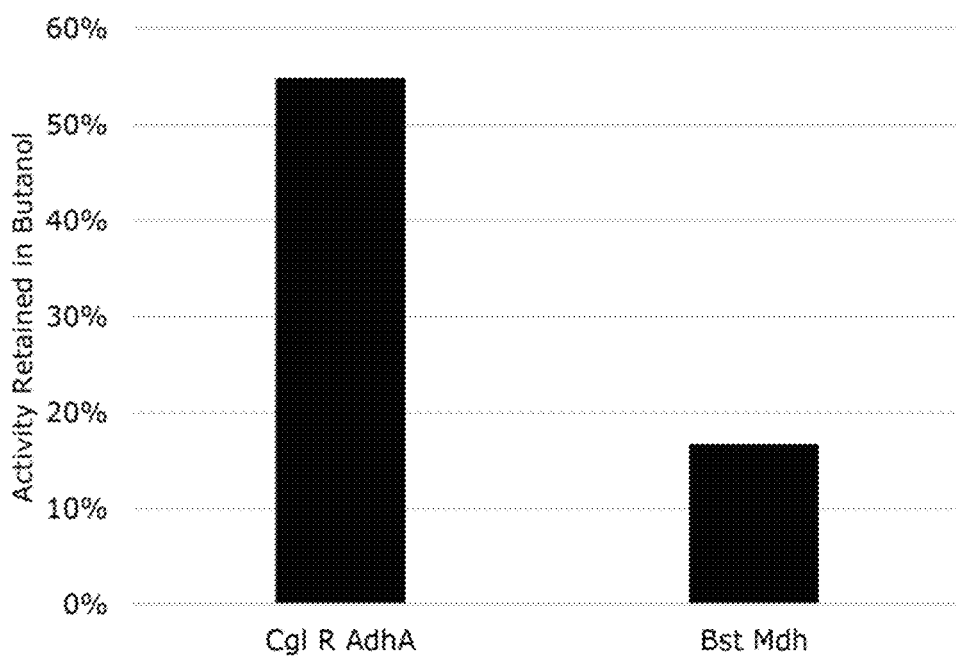
FIG. 13 shows the amount of in vivo specific methanol oxidation activity retained in the presence of butanol in recombinant *Escherichia coli* cell suspensions. Recombinant *Escherichia coli* cells expressing either *Bacillus stearothermophilus* 2334 (Bst) methanol dehydrogenase (Mdh) or *Corynebacterium glutamicum* R (Cgl R) alcohol dehydrogenase A (AdhA) were first grown to a dense concentration in rich media and then resuspended in a minimal media containing 60 millimolar (mM) methanol (MeOH) as the only carbon source or 60 millimolar (mM) methanol (MeOH) and 10 millimolar (mM) n-butanol (BuOH) as the only carbon sources. Specific activity of methanol oxidation was calculated as the slope of initial formaldehyde (HCHO) formation normalized to biomass concentration. Specific activity retained in butanol was calculated by dividing the specific activities of cultures containing methanol and butanol by those of cultures containing only methanol. Cgl R AdhA retained a higher percentage of specific methanol oxidation activity compared to Bst Mdh, as indicated. This suggests that methanol oxidation of Cgl R AdhA is less inhibited by butanol than that of Bst Mdh, suggesting Cgl R AdhA has a higher affinity, and thus a lower Km value, for methanol than butanol, which has been verified in the literature though in vitro characterization.

Example 5. Cloning the Complete Ribulose Monophosphate (RuMP) Pathway in E. coli Given the previous data, it appears that in order for E. coli to be able to utilize methanol without stimulation additional carbon sources, it must be able to regenerate ribulose-5-phosphate (Ru5P) in order to utilize the RuMP pathway. To achieve this goal, we were inspired by the methylotrophic organism *Bacillus methanolicus*, which utilizes the RuMP pathway for growth on MeOH. In this organism, growth on MeOH is plasmid dependent, as these organisms harbor a plasmid that carries an mdh gene as well as five homologues of the pentose phosphate pathway genes (pfk, phosphofructokinase; fba, fructose bisphosphate aldolase; tkt, transketolase; glpX, fructose/sedoheptulose biphosphatase; rpe, ribulose phosphate epimerase). When the strain is cured of the plasmid, it loses the ability to grow on methanol. This has been shown to be due to the loss of the five PPP homologues instead of loss of the MDH. Thus, we hypothesize that expression of the five genes from *B. methanolicus* in E. coli along with expression of MDH, HPS, and PHI will allow for the cells to regenerate ribulose-5-phosphate and thus grow utilizing methanol as the sole carbon and energy source. To that end, we had the five genes from synthesized and optimized for expression in E. coli. We integrated the five heterologous genes into the chromosome of E. coli in two operons; one operon contained rpe and tkt and the other operon contained fba, glpX and pfk. Cells were grown in minimal media containing 1 gram per liter of yeast extract and supplemented with methanol as a co-substrate. As illustrated in FIGS. 12 & 13, cultures supplemented with methanol demonstrate higher biomass yields compared with those not supplemented with methanol, and a higher depth of labeling in metabolites was observed when the five heterologous genes are present compared to when they are absent. This indicates that the five heterologous genes function to enhance methanol assimilation in a synthetic methylotrophic organism.

5.a. Genes for Metabolic Engineering to Enable E. coli to Grow Effectively on MeOH Methanol will be used as a carbon source by conversion to HCHO by a MeOH dehydrogenase (MDH). HCHO will then be converted to hexulose-6-phosphate, using ribulose-5-phosphate, by a hexulose phosphate synthase (HPS). Hexulose phosphate isomerase (PHI) will convert the hexulose-6-phosphate to fructose-6-phosphate, which can then be used for pyruvate generation that can be fed into the n-BuOH producing pathway (FIG. 2 of WO 2015/108777). There is strong experimental evidence supporting functionality of these genes, individually, in E. coli.

While we have previously demonstrated the MDH from *Bacillus stearothermophilus* can effectively oxidize methanol in recombinant E. coli, we anticipate issues with this enzyme will arise during the production of butanol. We have observed that the presence of butanol significantly decreases the ability of this enzyme to oxidize methanol. Therefore, we aim to employ MDH belonging the aforementioned Cgl-family. We have demonstrated these enzymes to be active in E. coli and also exhibit reduced sensitivity to the presence of butanol. Additionally, we propose protein engineering to increase the V max of these enymzes for MeOH, which we hypothesize will increase the rate of methanol oxidation/assimilation.

The next two enzymes, HPS and PHI, have also been successfully cloned into *E. coli*. Cell extracts of *E. coli* containing an expression plasmid with the *Bacillus subtilis* hps and phi genes were used to show good activity for these enzymes. Furthermore, $^{13}C$ NMR demonstrated that HCHO was incorporated into hexulose-6-phosphate and fructose-6-phosphate. In addition, the hps and phi cluster from *B. brevis* S1 was cloned into *E. coli* to demonstrate good HPS and PHI activities. More recently, a gene coding for an HPS-PHI fusion from *Mycobacterium gastri* MB19 was expressed in *E. coli* and cells were able to metabolize HCHO added to the culture and continue growing. We have also included the *Methylococcus capsulatus* MCA2738 gene that is annotated to have HPS and PHI activities, as another option to investigate. Combined, these data strongly suggest that expression of MDH, HPS and PHI expression in *E. coli* is feasible and can facilitate the formation of F6P from MeOH through HCHO via the RuMP pathway. We will first express these genes alone, test in vitro activities, choose the genes that lead to the two highest activities and then express these genes combinatorially aiming to identify at least 2 combinations of the 3 genes that give the best growth on MeOH prior to pursuing Tasks 3 and 4. Effectiveness is assessed by the rate of growth on MeOH and final densities (by optical density (OD) measurements), as well as rates of MeOH utilization (by GC and/or HPLC). We will also examine metabolites (acetate, ethanol, higher carboxylic acids; by HPLC) that will likely be produced anaerobically until we engineer this module into the n-BuOH producing strain. Strategies for expressing these genes are discussed below. The Gibson assembly method enables quick plasmid construction for screening to identify the best genes and the best combinations.

5.b. Integrate Optimized Modules 1, 2 and 3 (FIG. 2 of WO 2015/108777) to Achieve Effective MeOH Utilization, CO2 Fixation and n-BuOH Formation.

The assembled Modules 1 and 2 (FIG. 2 of WO 2015/108777) will be optimized to achieve high rates of MeOH and $CO_2$ utilization and n-BuOH formation. The goal is to integrate and further optimize these pathways by combing the best of these into a single strain that does not produce BuOH and later after some testing, into a BuOH producing strain. We will then employ chemical mutagenesis and strain evolution to achieve better growth on MeOH, $CO_2$ fixation and n-BuOH production. BuOH producing strain contains several gene deletions aiming to enhance the electron availability for BuOH production under anaerobic conditions. The strain then expresses a clostridial pathway for n-BuOH, with the genes expressed from co-existing plasmids. With the additional genes (FIG. 2 of WO 2015/108777) that will be needed here, we will need to integrate several of the genes from Modules 1 and 3 (FIG. 2 of WO 2015/108777) and possibly from the BuOH-formation pathway into the chromosome. What will be integrated will be based on mRNA expression levels that we will measure by qRT-PCR. We have employed chromosomal integrations of multiple genes into the *E. coli* genome using the lambda-red system, so we will use these methods for chromosomal integration of genes. Strains that combine all 3 modules (FIG. 2 of WO 2015/108777) will be tested for growth on MeOH, $CO_2$ fixation and BuOH production. A few of the best performing strains will be evolved through chemical mutagenesis and fast transfer for faster growth on MeOH anaerobically under a $CO_2$ and also $H_2$ atmosphere (3 atm) is serum vials used to grow acetogens on gas mixtures of $CO_2/CO/H_2$. The $CO_2$ and $H_2$ pressure is to stimulate $CO_2$ uptake under a reducing environment and is meant to simulate the large-scale process where a large $CO_2$ pressure will be built during the anaerobic fermentation. A few of the best performing strains with gene integrations and accumulated mutations will be sequenced by the new PacBio technology. The goal will be to examine the mutations that improve the phenotype.

Example 6. Bioenergetic and Pathway Analysis 6.a. Conversion of Methanol to Acetyl-CoA and Butanol We will engineer *E. coli* cells to utilize MeOH as a carbon and energy source in an engineered RuMP pathway. To meet ARPA-E yield and energy efficiency we will use $CO_2$ recycling by Schemes 1 or 2 (or 3 if necessary) (FIG. 2 of WO 2015/108777). In Scheme 1, $CO_2$ is reduced to formate and then HCHO (rxn 2 of FIG. 2 of WO 2015/108777) that can be assimilated through the RuMP pathway. Scheme 2 utilizes the rTCA cycle. Backup Scheme 3 uses the glycine cleavage pathway via the glycine synthase. While Schemes 2 and 3 are not as ATP efficient (see rxn 3 of FIG. 2 of WO 2015/108777) as Scheme 1, ATP hydrolysis improves the overall thermodynamic outlook of $CO_2$ fixation. Maximum theoretical yields were calculated per ARPA-E instructions for the engineered RuMP pathway with $CO_2$ recycling through either Scheme 1, 2 or 3 (Table 4). In both cases (Scheme 1; Scheme 2 or 3), the calculated yields outperform the energy efficiency and carbon yield metrics of >64% and >67%, respectively, even if we assume that 80% (our target) of theoretically possible $CO_2$ is fixed (in fact ca. 67% of the theoretically possible $CO_2$ fixation would suffice).

6.b. The Rate of Product Formation

For producing n-BuOH, we will employ the recently reported system, which produces ca. 30 g/L n-BuOH, but at a rate <1 g/gCDW/h. To meet the latter rate, we will need to optimize all 3 modules (FIG. 2 of WO 2015/108777). We will first aim to achieve fluxes to acetyl-CoA that supports high fluxes of product formation for products synthesized through Acetyl-CoA. Then, we will assess the bottlenecks in Module 3 (BuOH synthesis) by relating flux data to mRNA levels of key genes to examine if gene expression of certain genes is limiting the flux. Based on flux data, mRNA data and enzyme assays, we will identify the steps that limit the overall rate, and will use an iterative optimization process to achieve the most efficient strain and process.

TABLE 1

Organisms containing NAD+-dependent MDHs with similar identity to *Corynebacterium glutamicum* R (Cgl R) alcohol dehydrogenase A (AdhA).

| Methanol Dehydrogenase [Organism] | Identity |
|---|---|
| zinc-dependent alcohol dehydrogenase [*Corynebacterium glutamicum*] | 100% |
| MULTISPECIES: zinc-dependent alcohol dehydrogenase [*Corynebacterium*] | 99% |
| alcohol dehydrogenase [*Corynebacterium glutamicum*] | 99% |
| alcohol dehydrogenase AdhP [*Corynebacterium glutamicum*] | 99% |
| MULTISPECIES: zinc-dependent alcohol dehydrogenase [*Corynebacterium*] | 99% |

TABLE 1-continued

Organisms containing NAD$^+$-dependent MDHs with similar identity to
*Corynebacterium glutamicum* R (Cgl R) alcohol dehydrogenase A (AdhA).

| Methanol Dehydrogenase [Organism] | Identity |
|---|---|
| Zn-dependent alcohol dehydrogenase [*Corynebacterium glutamicum*] | 98% |
| MULTISPECIES: alcohol dehydrogenase [*Corynebacterium*] | 99% |
| zinc-dependent alcohol dehydrogenase [*Corynebacterium glutamicum*] | 99% |
| zinc-dependent alcohol dehydrogenase [*Corynebacterium glutamicum*] | 98% |
| zinc-dependent alcohol dehydrogenase [*Corynebacterium glutamicum*] | 98% |
| zinc-dependent alcohol dehydrogenase [*Corynebacterium crudilactis*] | 96% |
| zinc-dependent alcohol dehydrogenase [*Corynebacterium deserti*] | 97% |
| zinc-dependent alcohol dehydrogenase [*Corynebacterium lubricantis*] | 90% |
| zinc-dependent alcohol dehydrogenase [*Corynebacterium callunae*] | 91% |
| zinc-dependent alcohol dehydrogenase [*Corynebacterium stationis*] | 90% |
| zinc-dependent alcohol dehydrogenase [*Corynebacterium casei*] | 88% |
| zinc-dependent alcohol dehydrogenase [*Corynebacterium ammoniagenes*] | 87% |
| alcohol dehydrogenase [*Corynebacterium stationis*] | 87% |
| zinc-dependent alcohol dehydrogenase [*Corynebacterium casei*] | 87% |
| zinc-dependent alcohol dehydrogenase [*Corynebacterium amycolatum*] | 81% |
| zinc-dependent alcohol dehydrogenase [*Corynebacterium* sp. HMSC064E07] | 81% |
| zinc-dependent alcohol dehydrogenase [*Corynebacterium lactis*] | 81% |
| MULTISPECIES: zinc-dependent alcohol dehydrogenase [*Corynebacterium*] | 81% |
| MULTISPECIES: zinc-dependent alcohol dehydrogenase [*Corynebacterium*] | 81% |
| MULTISPECIES: zinc-dependent alcohol dehydrogenase [*Corynebacterium*] | 81% |
| zinc-dependent alcohol dehydrogenase [*Corynebacterium* sp. HMSC077G07] | 81% |
| zinc-dependent alcohol dehydrogenase [*Corynebacterium* sp. HMSC074C05] | 81% |
| zinc-dependent alcohol dehydrogenase [*Corynebacterium humireducens*] | 80% |
| zinc-dependent alcohol dehydrogenase [*Corynebacterium resistens*] | 80% |
| MULTISPECIES: zinc-dependent alcohol dehydrogenase [*Corynebacterium*] | 80% |
| zinc-dependent alcohol dehydrogenase [*Corynebacterium vitaeruminis*] | 78% |
| zinc-dependent alcohol dehydrogenase [*Corynebacterium durum*] | 78% |
| Alcohol dehydrogenase GroES-like protein [*Corynebacterium ulcerans*] | 78% |
| Alcohol dehydrogenase GroES-like protein [*Corynebacterium ulcerans* FRC11] | 78% |
| Alcohol dehydrogenase GroES-like protein [*Corynebacterium ulcerans*] | 78% |
| alcohol dehydrogenase [*Corynebacterium ulcerans* NCTC 12077] | 78% |
| Alcohol dehydrogenase GroES-like protein [*Corynebacterium ulcerans*] | 78% |
| Alcohol dehydrogenase GroES-like protein [*Corynebacterium ulcerans* FRC58] | 78% |
| zinc-dependent alcohol dehydrogenase [*Corynebacterium ulcerans*] | 77% |
| zinc-dependent alcohol dehydrogenase [*Corynebacterium ulcerans*] | 77% |
| zinc-dependent alcohol dehydrogenase [*Corynebacterium ulcerans*] | 77% |
| zinc-dependent alcohol dehydrogenase [*Corynebacterium efficiens*] | 79% |
| alcohol dehydrogenase [*Corynebacterium ulcerans* 0102] | 78% |
| zinc-dependent alcohol dehydrogenase [*Corynebacterium terpenotabidum*] | 78% |
| zinc-dependent alcohol dehydrogenase [*Corynebacterium lipophiloflavum*] | 79% |
| zinc-dependent alcohol dehydrogenase [*Corynebacterium diphtheriae*] | 81% |
| zinc-dependent alcohol dehydrogenase [*Corynebacterium diphtheriae*] | 81% |
| MULTISPECIES: zinc-dependent alcohol dehydrogenase [*Corynebacterium*] | 78% |
| zinc-dependent alcohol dehydrogenase [*Corynebacterium* sp. HMSC034A01] | 76% |
| zinc-dependent alcohol dehydrogenase [*Corynebacterium* sp. HMSC034B08] | 77% |
| zinc-dependent alcohol dehydrogenase [*Corynebacterium* sp. HMSC05H05] | 77% |
| zinc-dependent alcohol dehydrogenase [*Corynebacterium mustelae*] | 78% |
| zinc-dependent alcohol dehydrogenase [*Corynebacterium* sp. HMSC04H06] | 78% |
| zinc-dependent alcohol dehydrogenase [*Corynebacterium pseudotuberculosis*] | 76% |
| alcohol dehydrogenase AdhP [*Corynebacterium diphtheriae*] | 80% |
| zinc-dependent alcohol dehydrogenase [*Corynebacterium* sp. HMSC070H05] | 76% |
| zinc-dependent alcohol dehydrogenase [*Corynebacterium* sp. HMSC29G08] | 76% |
| MULTISPECIES: zinc-dependent alcohol dehydrogenase [*Corynebacterium*] | 76% |
| zinc-dependent alcohol dehydrogenase [*Corynebacterium diphtheriae*] | 80% |
| zinc-dependent alcohol dehydrogenase [*Corynebacterium pseudotuberculosis*] | 76% |
| zinc-dependent alcohol dehydrogenase [*Corynebacterium* sp. HMSC11D10] | 76% |
| zinc-dependent alcohol dehydrogenase [*Corynebacterium diphtheriae*] | 80% |
| zinc-dependent alcohol dehydrogenase [*Corynebacterium kutscheri*] | 76% |
| zinc-dependent alcohol dehydrogenase [*Corynebacterium diphtheriae*] | 80% |
| zinc-dependent alcohol dehydrogenase [*Corynebacterium freiburgense*] | 77% |
| alcohol dehydrogenase [*Corynebacterium pseudotuberculosis* FRC41] | 76% |
| zinc-dependent alcohol dehydrogenase [*Corynebacterium* sp. HMSC067D03] | 76% |
| zinc-dependent alcohol dehydrogenase [*Corynebacterium* sp. HMSC036E10] | 76% |
| zinc-dependent alcohol dehydrogenase [*Corynebacterium jeddahense*] | 75% |
| zinc-dependent alcohol dehydrogenase [*Corynebacterium ciconiae*] | 79% |
| alcohol dehydrogenase, propanol-preferring [*Corynebacterium coyleae*] | 76% |
| zinc-dependent alcohol dehydrogenase [*Corynebacterium sputi*] | 77% |
| zinc-dependent alcohol dehydrogenase [*Corynebacterium pseudotuberculosis*] | 76% |
| zinc-dependent alcohol dehydrogenase [*Corynebacterium tuscaniense*] | 76% |
| alcohol dehydrogenase AdhP [*Corynebacterium diphtheriae*] | 80% |
| zinc-dependent alcohol dehydrogenase [*Corynebacterium* sp. HMSC074A01] | 76% |
| zinc-dependent alcohol dehydrogenase [*Corynebacterium variabile*] | 78% |
| alcohol dehydrogenase AdhP [*Corynebacterium pseudotuberculosis*] | 75% |
| zinc-dependent alcohol dehydrogenase [*Corynebacterium nuruki*] | 78% |
| zinc-dependent alcohol dehydrogenase [*Corynebacterium testudinoris*] | 77% |

TABLE 1-continued

Organisms containing NAD⁺-dependent MDHs with similar identity to
*Corynebacterium glutamicum* R (Cgl R) alcohol dehydrogenase A (AdhA).

| Methanol Dehydrogenase [Organism] | Identity |
|---|---|
| Alcohol dehydrogenase [*Corynebacterium striatum*] | 77% |
| zinc-dependent alcohol dehydrogenase [*Corynebacterium pseudodiphtheriticum*] | 76% |
| MULTISPECIES: alcohol dehydrogenase [*Corynebacterium*] | 77% |
| MULTISPECIES: zinc-dependent alcohol dehydrogenase [*Corynebacterium*] | 77% |
| zinc-dependent alcohol dehydrogenase [*Corynebacterium* sp. EPI-003-04-2554_SCH2473622] | 76% |
| zinc-dependent alcohol dehydrogenase [*Corynebacterium* sp. HMSC06C06] | 76% |
| zinc-dependent alcohol dehydrogenase [*Corynebacterium* sp. SN15] | 76% |
| zinc-dependent alcohol dehydrogenase [*Corynebacterium pseudodiphtheriticum*] | 76% |
| zinc-dependent alcohol dehydrogenase [*Corynebacterium propinquum*] | 73% |
| MULTISPECIES: zinc-dependent alcohol dehydrogenase [*Corynebacterium*] | 73% |
| zinc-dependent alcohol dehydrogenase [*Corynebacterium* sp. KPL1818] | 73% |
| hypothetical protein HMPREF1267_01835 [*Corynebacterium* sp. KPL1824] | 74% |
| zinc-dependent alcohol dehydrogenase [*Corynebacterium timonense*] | 73% |
| zinc-dependent alcohol dehydrogenase [*Corynebacterium* sp. KPL1824] | 73% |
| alcohol dehydrogenase, propanol-preferring [*Cryobacterium flavum*] | 70% |
| alcohol dehydrogenase, propanol-preferring [*Cryobacterium luteum*] | 71% |
| alcohol dehydrogenase, propanol-preferring [*Cryobacterium levicorallinum*] | 69% |
| zinc-dependent alcohol dehydrogenase [*Arthrobacter* sp. 162MFSha1.1] | 71% |
| zinc-dependent alcohol dehydrogenase [*Rothia* sp. ND6WE1A] | 68% |
| alcohol dehydrogenase [*Arthrobacter* sp. Soil761] | 71% |

TABLE 2

Reaction Gibbs energies ($\Delta_r G$), equilibrium constants ($K_{eq}$), and change in reduction potential ($\Delta\varepsilon$) for MeOH redox reactions calculated through eQuilibrator software. Standard conditions were 25° C., 1 bar, pH 7.0, 0.1 M ionic strength, and 1 mM species concentrations. Physiological conditions were the indicated temperatures, 1 bar, pH 7.6, 0.1 M ionic strength, 1250 mM MeOH, 0.17 mM HCHO, 2.6 mM NAD, 0.083 mM NADH. Data were calculated from the following equations:
$\Delta_r G = -n(23,064)\Delta\varepsilon$, where n represents the number of electrons transferred, $K_{eq} = 10^{-\Delta_r G'}/2.3 RT$, and $\Delta_r G = \Delta_r G' + RT \ln \frac{[P]}{[R]}$, where P and R indicate products and reactants, respectively. [a]Values in parentheses under physiological conditions were calculated with a 10-fold decrease in HCHO concentration, i.e., 0.017 mM. The discrepancy between some of the $\Delta_r G$ and $K_{eq}$ values for NAD-dependent oxidation is likely a result of the 95% confidence interval for $\Delta_r G$, which is ± 6.5 kJ/mol.

| | Standard Conditions | | | Physiological Conditions | | | |
|---|---|---|---|---|---|---|---|
| Methanol Redox Reaction | $\Delta\varepsilon'$ (mV) | $\Delta_r G'$ (kJ/mol) | $K'_{eq}$ | T (° C.) | $\Delta\varepsilon$(mV) | $\Delta_r G$ (kJ/mol) | $K_{eq}$ |
| CH₃OH + NAD ⇔ HCHO + NADH + H⁺ | −177 | +34.2 | 1.0 × 10⁻⁶ | 37 | +5.3 (+36.1)[a] | −1.0 (−7.0)[a] | 0.925 (8.5)[a] |
| | | | | 45 | +9.6 (+41.1)[a] | −1.8 (−7.9)[a] | 0.927 (8)[a] |
| | | | | 55 | +14.9 (+47.4)[a] | −2.9 (−9.2)[a] | 0.929 (7.5)[a] |

TABLE 3

MDH in vitro enzyme kinetics.

| | Km (mM) | | | | Vmax (μmol/min · mg) | | | |
|---|---|---|---|---|---|---|---|---|
| | MeOH | EtOH | n-PrOH | n-BuOH | MeOH | EtOH | n-PrOH | n-BuOH |
| Cgl AdhA | 3 | 6.8 | 7.5 | 35 | 0.7 | 7.8 | 7.7 | 8.9 |
| Bst Mdh | 20 | 0.08 | 0.02 | 0.01 | 2.1 | — | — | — |
| Bme Mdh3 | 200 | — | — | — | 0.07 | 2 | 3.5 | 2.3 |

TABLE 4

Bioenergetic and pathway analysis.

| | CO$_2$ fixation | | | | | | | |
|---|---|---|---|---|---|---|---|---|
| | Scheme 1 | | | | Scheme 2 or 3 | | | |
| | CH$_4$ Act. Scheme* | | | | | | | |
| | I | II | III# | IV | I | II | III# | IV |
| Methane | −100.0 | −100.0 | −100.0 | −100.0 | −100.0 | −100.0 | −100.0 | −100.0 |
| CO$_2$ | 0.0 | 16.7 | 33.3 | −33.3 | 0.0 | 16.7 | 33.3 | 0.0 |
| NAD(P)H | 0.0 | 0.0 | 0.0 | 0.0 | 0.0 | 0.0 | 0.0 | 100.0 |
| ATP | 50.0 | 41.7 | 33.3 | 66.7 | 0.0 | 16.7 | 33.3 | 0.0 |
| Butanol | 25.0 | 20.8 | 16.7 | 33.3 | 25.0 | 20.8 | 16.7 | 25.0 |
| Energy Efficiency | 77% | 64% | 51% | 102% | 77% | 64% | 51% | 77% |
| Carbon Yield | 100% | 83% | 67% | 133% | 100% | 83% | 67% | 100% |

*See FIG. 1 of WO 2015/108777 and text for CH$_4$ activation schemes.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A non-naturally occurring microbe capable of growing in a medium comprising methanol, comprising a heterologous polynucleotide encoding a heterologous methanol dehydrogenase (MDH) from a *Corynebacterium* organism (Cor), wherein the microbe expresses the heterologous MDH and one or more heterologous ribulose monophosphate (RuMP) pathway enzymes, wherein the heterologous MDH consists of the amino acid sequence of SEQ ID NO: 1, wherein the one or more RuMP pathway enzymes comprise heterologous 3-hexulose-6-phosphate synthase (HPS) and heterologous 3-hexulose-6-phosphate isomerase (PHI), and wherein the non-naturally occurring microbe is *E. coli*.

2. The non-naturally occurring microbe of claim 1, wherein the Cor is selected from the group consisting of *Corynebacterium glutamicum, Corynebacterium sp., Corynebacterium crudilactis, Corynebacterium deserti, Corynebacterium lubricantis, Corynebacterium callunae, Corynebacterium stationis, Corynebacterium casei, Corynebacterium ammoniagenes, Corynebacterium amycolatum, Corynebacterium* sp. HMSC064E07, *Corynebacterium lactis, Corynebacterium* sp. HMSC077G07, *Corynebacterium* sp. HMSC074C05, *Corynebacterium humireducens, Corynebacterium resistens, Corynebacterium vitaeruminis, Corynebacterium durum, Corynebacterium ulcerans, Corynebacterium ulcerans* FRC11, *Corynebacterium ulcerans* NCTC 12077, *Corynebacterium ulcerans* FRC58, *Corynebacterium efficiens, Corynebacterium ulcerans* 0102, *Corynebacterium terpenotabidum, Corynebacterium lipophiloflavum, Corynebacterium diphtheria, Corynebacterium* sp. HMSC034A01, *Corynebacterium* sp. HMSC034B08, *Corynebacterium* sp. HMSC05H05, *Corynebacterium mustelae, Corynebacterium* sp. HMSC04H06, *Corynebacterium pseudotuberculosis, Corynebacterium* sp. HMSC070H05, *Corynebacterium* sp. HMSC29G08, *Corynebacterium* sp. HMSC11D10, *Corynebacterium kutscheri, Corynebacterium freiburgense, Corynebacterium pseudotuberculosis* FRC41, *Corynebacterium* sp. HMSC067D03, *Corynebacterium* sp. HMSC036E10, *Corynebacterium jeddahense, Corynebacterium ciconiae, Corynebacterium coyleae, Corynebacterium sputi, Corynebacterium tuscaniense, Corynebacterium* sp. HMSC074A01, *Corynebacterium variabile, Corynebacterium nuruki, Corynebacterium testudinoris, Corynebacterium striatum, Corynebacterium pseudodiphtheriticum, Corynebacterium* sp. EPI-003-04-2554_SCH2473622, *Corynebacterium* sp. HMSC06C06, *Corynebacterium* sp. SN15, *Corynebacterium propinquum, Corynebacterium* sp. KPL1818, *Corynebacterium* sp. KPL1824, *Corynebacterium timonense, Corynebacterium* sp. KPL1824, *Cryobacterium flavum, Cryobacterium luteum, Cryobacterium levicorallinum, Arthrobacter* sp. 162MFSha1.1, *Rothia* sp. ND6WE1A, and *Arthrobacter* sp. Soil761.

3. The non-naturally occurring microbe of claim 1, wherein the Cor is a *Corynebacterium glutamicum* (Cgl).

4. The non-naturally occurring microbe of claim 1, wherein the methanol contributes to at least 40% of the carbon source for the non-naturally occurring microbe.

5. The non-naturally occurring microbe of claim 1, wherein the expression of the one or more RuMP pathway enzymes is under control of a formaldehyde responsive promoter.

6. The non-naturally occurring microbe of claim 1, further expressing one or more heterologous pentose-phosphate pathway (PPP) enzymes.

7. The non-naturally occurring microbe of claim 6, wherein the expression of the one or more heterologous PPP enzymes is under control of a formaldehyde responsive promoter.

8. The non-naturally occurring microbe of claim 6, wherein the one or more heterologous PPP enzymes comprise heterologous phosphofructokinase (PFK), heterologous fructose bisphosphate aldolase (FBA), heterologous transketolase (TKT), heterologous fructose/sedoheptulose biphosphatase (GLPX), heterologous transaldolase (TAL), heterologous ribose-5-phosphate isomerase (RPI) and heterologous ribulose phosphate epimerase (RPE).

9. The non-naturally occurring microbe of claim 1, wherein the non-naturally occurring microbe comprises a deletion of a frmRAB operon.

10. A method for oxidizing methanol, comprising growing the non-naturally occurring microbe of claim 1 in a medium comprising methanol, whereby the methanol is oxidized.

11. The method of claim 10, further comprising producing a metabolite.

12. The method of claim 11, wherein the metabolite is n-butanol.

13. The method of claim 11, wherein the metabolite is selected from the group consisting of 4-carbon chemicals, diacids, 3-carbon chemicals, higher carboxylic acids, alcohols of higher carboxylic acids, polyhydroxyalkanoates, and specialty chemicals.

14. The method of claim 13, wherein the 4-carbon chemicals are selected from the group consisting of butyrate, n-butanol, i-butanol, 2-butanol, 2,3-butanediol, and 1,4-butanediol.

15. The method of claim 13, wherein the diacids are selected from the group consisting of oxalic, malonic, succinic, glutaric, adipic, pimelic, phthalic, isophthalic, and terephthalic.

16. The method of claim 13, wherein the 3-carbon chemicals are selected from the group consisting of propanol, propanediol, lactate, and acrylate.

17. The method of claim 13, wherein the higher carboxylic acids are selected from the group consisting of pentanoic acids and hexanoic acids.

18. The method of claim 13, wherein the specialty chemicals are selected artemisinin, vanillin, anthocyanins and resveratrol.

* * * * *